United States Patent
Hale et al.

(12) 
(10) Patent No.: US 6,323,178 B1
(45) Date of Patent: *Nov. 27, 2001

(54) BETA-LIPOTROPIN METHODS

(75) Inventors: John Edward Hale, Fishers; Mark Louis Heiman, Indianapolis; Brigitte Elisabeth Schoner, Monrovia; William Francis Heath, Jr., Fishers, all of IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/217,228

(22) Filed: Dec. 21, 1998

Related U.S. Application Data

(60) Provisional application No. 60/068,659, filed on Dec. 23, 1997, provisional application No. 60/079,857, filed on Mar. 30, 1998, provisional application No. 60/086,321, filed on May 21, 1998, provisional application No. 60/091,385, filed on Jul. 1, 1998, provisional application No. 60/095,405, filed on Aug. 5, 1998, and provisional application No. 60/103,976, filed on Oct. 13, 1998.

(51) Int. Cl.$^7$ ............................ A61K 38/04; A61K 38/16
(52) U.S. Cl. ..................................... 514/12; 514/2; 514/8; 514/13; 514/14; 514/15
(58) Field of Search .............................. 514/12, 8, 2, 13, 514/14, 15

(56) References Cited

U.S. PATENT DOCUMENTS

| | | | |
|---|---|---|---|
| 4,769,326 | 9/1988 | Rutter et al. | 435/68 |
| 5,258,496 | 11/1993 | Benson et al. | 530/350 |
| 5,691,309 | 11/1997 | Basinski et al. | 514/12 |

FOREIGN PATENT DOCUMENTS

WO 95/07697   3/1995  (WO) .

OTHER PUBLICATIONS

Smith, D., et al., "Single Step Purification of Polypeptides Expressed in *Escherichia coli* as Fusions With Glutathione S–transferase," *Gene*, 67:31–40, 1998.

Bielmann, P., et al., "Lipogenic Activity of a Potent Lipolytic Hormone: Sheep βLipotropin (β–LPH). II. Further Effects of Sheep (β–LPH) on Specifically Labeled Glucose and the Localization of Lipogenic Active Center of the Molecule", *Horm. Metab. Res.* 4:22–25, 1972.

Li, C., et al. "Isolation, characterization and Amino Acid Sequence of β Lipotropin From Human Pituitary Glands", *Int. J. Peptide Protein Res.* 17:131–142, 1981.

Takahashi et al. FEBS Lett. 135:97–102, Nov. 1981.*

Callard et al. The Cytokine FactsBook. Academic Press, London, p. 31, 1994.*

Bowie et al. Science 247:1306–1310, 1990.*

Wells. Biochemisrty 29:8509–8517, 1990.*

Ngo et al. The Protein Folding Problem and Tertiary Structure Prediction Merz et al., eds., Birkhauser, Boston, pp. 492–495, Nov. 1981.*

* cited by examiner

*Primary Examiner*—Elizabeth Kemmerer
(74) *Attorney, Agent, or Firm*—Thomas D. Webster

(57) ABSTRACT

The invention provides isolated nucleic acids, vectors, transformed host cells, analogs, functional fragments, and fusion proteins, related to beta-lipotropin. Also provided are pharmaceutical compositions comprising beta-lipotropin or fragments and/or analogs thereof, and methods for treating diabetes and complications associated therewith by administration of an effective amount of beta-lipotropin.

19 Claims, 17 Drawing Sheets

FIG.1

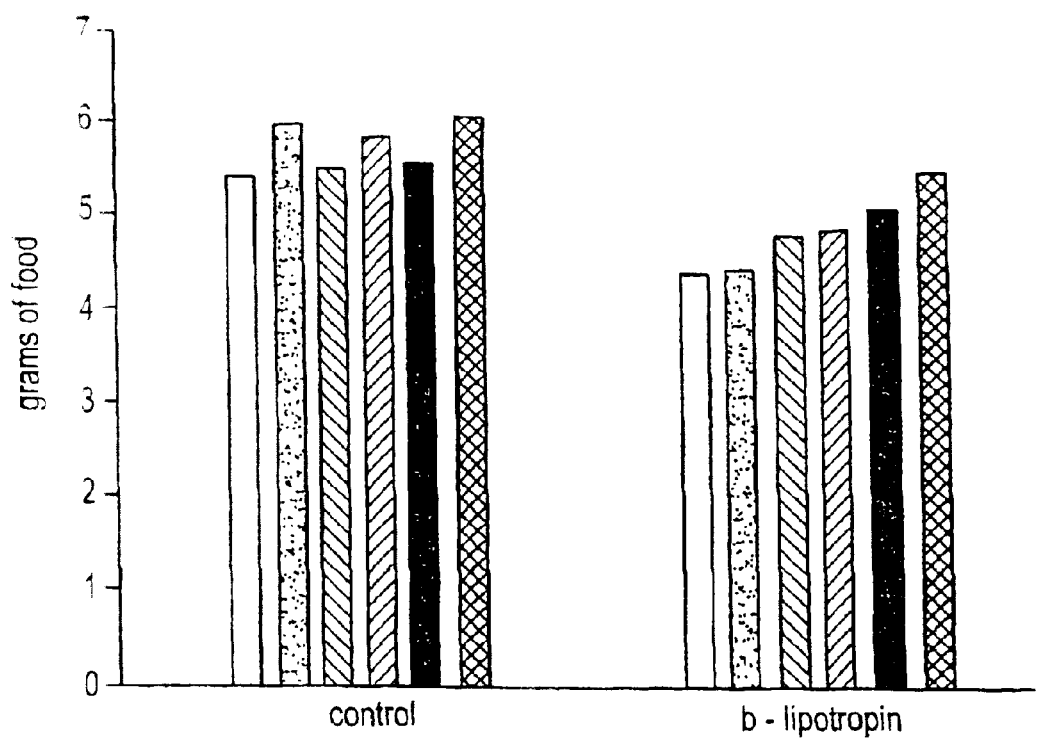

☐ grams of food eaten in 1 day before administration of b - lipotropin or vehicle
▨ grams of food eaten day 1 after administration of b - lipotropin or vehicle
▨ grams of food eaten day 2 after administration of b - lipotropin or vehicle
▨ grams of food eaten day 3 after administration of b - lipotropin or vehicle
■ grams of food eaten day 4 after administration of b - lipotropin or vehicle
▨ grams of food eaten day 5 after administration of b - lipotropin or vehicle

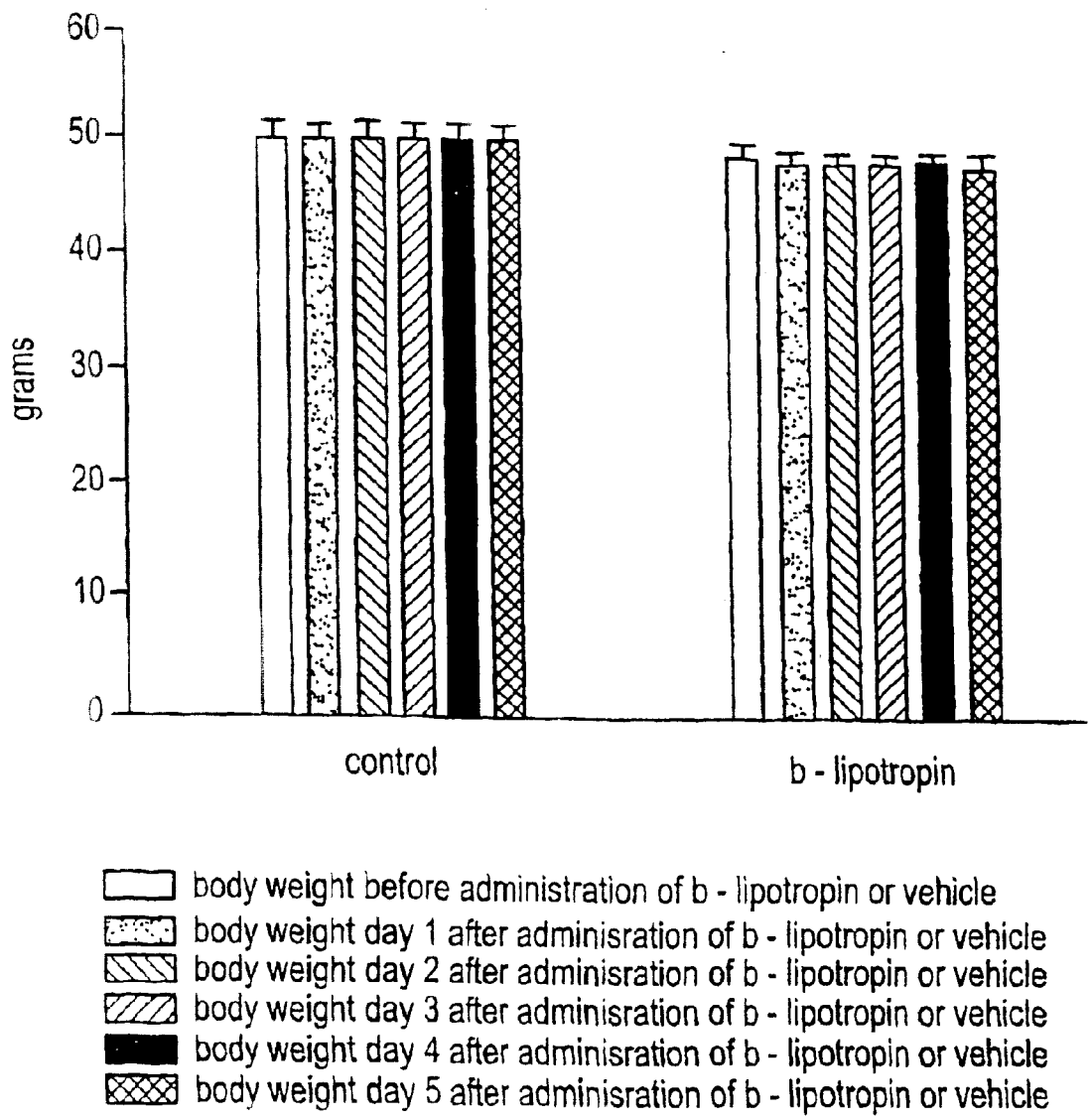

BETA-LIPOTROPIN METHODS

CROSS-REFERENCE

This application claims the benefit of U.S. Provisional Application No. 60/068,659, filed Dec. 23, 1997; No. 60/079,857, filed Mar. 30, 1998; No. 60/086,321, filed May 21, 1998; No. 60/091,385, filed Jul. 1, 1998; No. 60/095,405, filed Aug. 5, 1998; and No. 60/103,976, filed Oct. 13, 1998.

BACKGROUND OF THE INVENTION

This invention relates to the pharmaceutical and medical arts. In particular the invention pertains to beta-lipotropin, fragments and analogs thereof, pharmaceutical formulations, and methods for using same in treating diabetes and other associated conditions in mammals.

Proopiomelanocortin (POMC) is a neuropeptide precursor molecule which is translocated to secretory pathways within neuroendocrine cells. POMC is cleaved by the action of specific endopeptidases to yield peptides such as adrenocorticotrophic hormone (ACTH), Beta-lipotropin (BLT), Beta-endorphin, and Melanocyte Stimulating Hormone (MSH). The processing of POMC into one or more specific peptides occurs in a tissue and cell specific manner (See generally, M. Castro and E. Morrison, *Crit. Rev. Neurobiol.*, 11, 35–57, 1997; Roberts, J. L. and Herbert, E., *Proc Nat Acad Sci*, 74, 4826 (1977); Roberts, J. L. and Herbert, E., *Proc.Nat.Acad.Sci* 74, 5300 (1977); Mains, et al., *Proc.Nat.Acad.Sci* 74, 3014 (1977)). POMC is produced mainly in the pituitary gland and hypothalamus. Post-translational processing of POMC in the anterior pituitary produces ACTH and BLT. On the other hand, the major products of the intermediate pituitary are $\alpha$-MSH, CLIP, $\gamma$-lipotropin, $\beta$-endorphin, and $\beta$-MSH, while in the hypothalamus, POMC is processed primarily into $\gamma$-MSH and $\beta$-endorphin.

POMC-derived peptides perform a variety of important roles in metabolic and physiological regulation. For example, ACTH, a 39 amino acid peptide, stimulates secretion of glucocorticoids from the adrenal cortex. The MSH's, on the other hand, stimulate melanin synthesis by melanocytes in the skin, and also appear to be involved in fat metabolism. $\beta$-endorphin derives from the carboxyl end of BLT (viz. Residues 59 to 89 of the human sequence), and possesses analgesic activity that is antagonized by naloxone, a known antagonist for morphine. Thus, POMC-derived peptide hormones have diverse roles in physiologic and metabolic regulation.

Proper glucose and fuel metabolism depend on the non-POMC related peptide, insulin. Specifically, insulin stimulates glycogen, fatty acid, and protein synthesis, and also stimulates glycolysis. Insulin is critical in promoting entry of glucose into muscle and fat cells.

Defective insulin metabolism may lead to diabetes. Type 1 diabetics require exogenous insulin administration for proper control of fuel and glucose metabolism. On the other hand, Type 2 diabetics typically do not require exogenous insulin until the later stages of the disease. Proper control of glucose and fuel metabolism is essential for effective management of diabetes. Without this, there can be serious, perhaps even fatal, consequences including ketoacidosis, coma, retinopathy, diabetic microangiopathy, atherosclerosis, myocardial infarction, stroke, gangrene, hypertriglyceridemia, hypercholesterolemia, cardiomyopathy, dermopathy, diabetic foot syndrome, nephropathy, urinary tract infection, papillary necrosis, cataracts, diabetic gastroenteropathy, constipation, peripheral vascular disease, and even death. In many instances, a delicate balance must be struck between administration of too much insulin and too little insulin. Therefore, an ideal therapy for diabetes would be one that controls blood glucose levels by improving sensitivity to insulin.

Described herein is a method for treatment and pharmaceutical composition that is effective in treating or preventing type 1 and type 2 diabetes, and associated complications thereof, comprising the administration of a pharmaceutically effective amount of beta-lipotropin and/or fragments and/or analogs thereof.

BRIEF SUMMARY OF THE INVENTION

The present invention provides isolated proteins comprising beta-lipotropin (BLT), analogs thereof, fragments thereof, nucleic acids encoding same, and methods for producing and using BLT in the treatment of diabetes and complications associated therewith.

Disclosed herein are methods for treating diabetes and complications thereof in mammals, including humans, by administering pharmaceutically effective amounts of BLT, analogs thereof, or functional fragments thereof. The invention relates further to methods of treatment for type 1 and type 2 diabetes, retinopathy, diabetic microangiopathy, atherosclerosis, myocardial infarction, stroke, gangrene, hypertriglyceridemia, hypercholesterolemia, cardiomyopathy, dermopathy, diabetic foot syndrome, nephropathy, urinary tract infection, papillary necrosis, cataracts, diabetic gastroenteropathy, constipation, and peripheral vascular disease.

Disclosed herein are methods for producing BLT in *E. coli* and yeast. In *E. coli* BLT is produced as a fusion protein which can be recovered from cell lysates in the presence of high salt by conventional purification methods. The BLT fusion protein contains a recognition site for specific proteases which are used to separate the fusion partner from BLT. In the yeast *Pichia pastoris*, the fusion protein is cleaved upon secretion of the protein from the cell such that native BLT can be recovered intact from the culture medium.

In one embodiment the present invention relates to a substantially pure protein having the amino acid sequence which is SEQ ID NO: 2, SEQ ID NO: 5, or SEQ ID NO: 7.

In still another embodiment the present invention relates to an isolated nucleic acid compound encoding a fusion protein or recombinant protein or peptide comprising beta lipotropin.

In another embodiment the present invention relates to at least one isolated nucleic acid compound encoding a protein or peptide of the present invention.

In still another embodiment the present invention relates to a vector comprising an isolated nucleic acid compound of the invention.

In yet another embodiment the present invention relates to a vector comprising an isolated nucleic acid of the invention, wherein said isolated nucleic acid compound is operably-linked to a promoter sequence.

In another embodiment the present invention relates to a host cell containing a vector of the present invention.

In yet another embodiment the present invention relates to a method for constructing a recombinant host cell having the potential to express beta-lipotropin, said method comprising introducing into said host cell by any suitable means a vector of the invention.

In still another embodiment the present invention relates to a method for expressing beta-lipotropin in a recombinant host cell, said method comprising culturing said recombinant host cell under conditions suitable for gene expression.

In another embodiment the present invention relates to a pharmaceutical formulation comprising as an active ingredient beta-lipotropin, analog, or functional fragment thereof, associated with one or more pharmaceutically acceptable carriers, excipients, or diluents therefor.

In still another embodiment the present invention relates to a pharmaceutical formulation wherein said beta-lipotropin, analog, or functional fragment thereof, is human beta-lipotropin.

In yet another embodiment the present invention relates to beta-lipotropin, analog, or functional fragment thereof, for use in treating diabetes or complications thereof.

In still another embodiment the present invention relates to fragments of BLT having insulinotropic activity.

In still another embodiment the present invention relates to a peptide having insulinotropic activity selected from the group consisting of SEQ ID NO:9 through SEQ ID NO:13.

In still another embodiment the present invention relates to a peptide having insulinotropic activity selected from the group consisting of SEQ ID NO:14 through SEQ ID NO:25.

In still another embodiment the present invention relates to a functional analog of a beta-lipotropin peptide disclosed herein.

In still another embodiment the present invention relates to a method for treating diabetes comprising administration of a therapeutically effective amount of at least one peptide selected from the group consisting of SEQ ID NO:9 through SEQ ID NO:25.

In still another embodiment the present invention relates to a method for treating diabetes comprising administration of a therapeutically effective amount of a peptide selected from the group consisting of SEQ ID NO:9 through SEQ ID NO:13.

In still another embodiment the present invention relates to a pharmaceutical formulation comprising as an active ingredient at least one peptide having insulinotropic activity selected from the group consisting of SEQ ID NO:9 through SEQ ID NO:25.

In still another embodiment the present invention relates to a method for treating diabetes in a mammal including a human comprising administration of a therapeutically effective amount of beta-lipotropin, analog, or functional fragment thereof.

In yet another embodiment the present invention relates to a method for lowering blood glucose levels in a mammal by administering an effective amount of beta-lipotropin, analog, or functional fragment thereof.

In yet another embodiment the present invention relates to a method for treating hyperglycemia in a mammal in need thereof by administering an effective amount of beta-lipotropin, analog, or functional fragment thereof.

In still another embodiment the present invention relates to a method for treating hyperinsulinemia in a mammal by administering an effective amount of beta-lipotropin, analog, or functional fragment thereof.

In another embodiment the present invention relates to a method for enhancing insulin sensitivity in a mammal by administering an effective amount of beta-lipotropin, analog, or functional fragment thereof.

In another embodiment the present invention relates to a solid-phase synthetic method for synthesizing beta-lipotropin, analog, or functional fragment thereof.

In another embodiment the present invention relates to a process for preparing beta-lipotropin comprising:
  a. transforming a suitable host with an expression vector wherein said vector encodes a beta-lipotropin, analog, or functional fragment thereof;
  b. culturing said transformed host under conditions that enable expression of said beta-lipotropin;
  c. purifying said beta-lipotropin by any suitable means.

In yet another embodiment the present invention relates to an assay for beta-lipotropin activity comprising the steps of:
  a) administering to a mammal that exhibits insulin insensitivity and elevated blood glucose levels a test protein; and
  b) testing for blood glucose and insulin levels after step (a).

The invention also relates to a method of treating type 1 or type II diabetes and complications associated therewith in mammals by the administration of a pharmaceutically effective amount of beta-lipotropin, analog, or functional fragment thereof.

BRIEF DESCRIPTION OF THE DRAWINGS

FIG. 1. Food consumption of male Avy/a mice during administration of mouse betalipotropin.

FIG. 2. Bodyweight of male Avy/a mice during administration of mouse betalipotropin.

DETAILED DESCRIPTION OF THE INVENTION

Definitions

Figure 3:
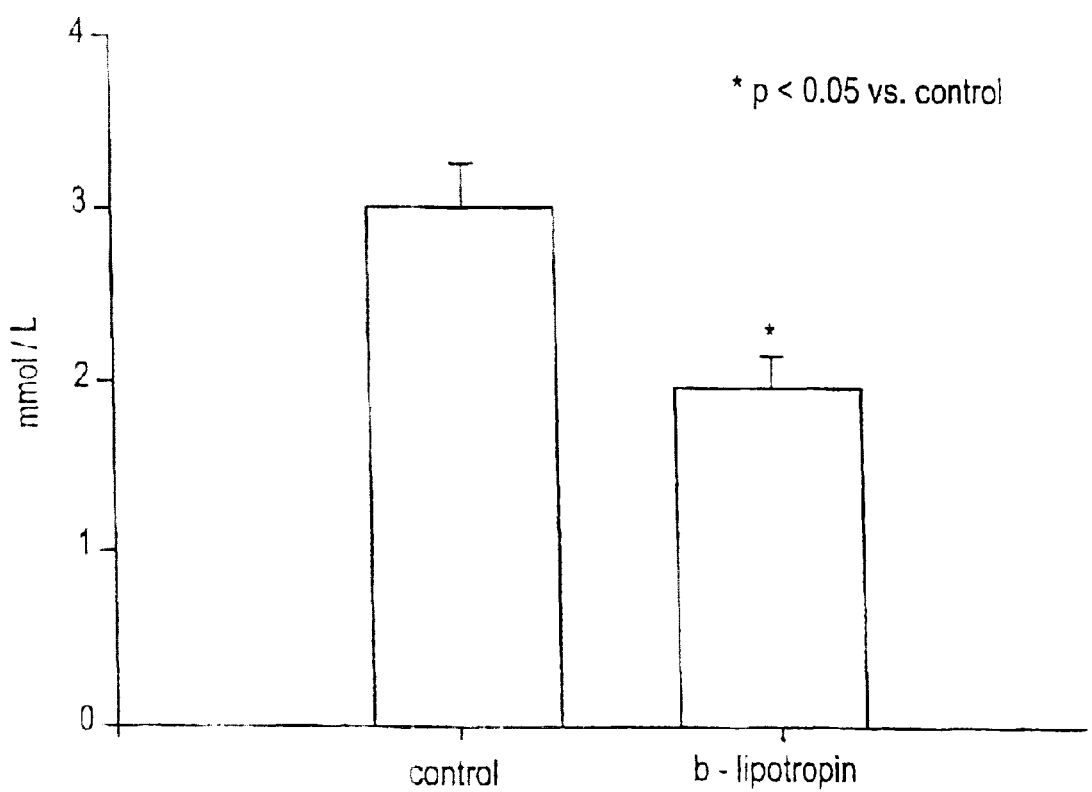
FIG. 3. Mouse betalipotropin decreases plasma triglycerides in male Avy/a mice after six days of administration.

The term "analog" or "functional analog" refers to a modified form of BLT in which at least one amino acid substitution has been made such that said analog retains substantially the same biological activity as the unmodified BLT in vivo and/or in vitro.

The term "bid" or "b.i.d." refers to a dosage of BLT or other compound administered twice daily.

"BLT" refers to beta-lipotropin. The human BLT comprises 89 amino acid residues (SEQ ID NO:8). The BLT protein has been characterized in a variety of organisms and the amino acid sequences determined in a variety of organisms including human, mouse, ovine, and porcine (Li & Chung, Nature, 260, 622–24 (1976); and elephant (Li et al. Int. J. Pept. Prot. Res. 32, 573–78, 1988); as well as other mammals, all of which are hereby incorporated by reference.

The term "beta-lipoprotein fusion protein" or "BLT fusion protein" refers to a class of hybrid recombinant protein molecules comprising BLT, that are produced in $E. coli$ or other cell type and from which can be generated BLT, or a BLT fragment through specific proteolysis or chemical cleavage. Exemplary BLT fusion proteins include those specified herein as SEQ ID NO:2, SEQ ID NO:5, and SEQ ID NO:7.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" means that the aforementioned relationship applies to substantially all base pairs comprising two single-stranded nucleic acid molecules over the entire length of said molecules. "Partially complementary" refers to the aforementioned relationship in which one of two single-stranded nucleic acid molecules is shorter in length than the other such that a portion of one of the molecules remains single-stranded.

The term "complications" or "complications thereof" as used herein refers to conditions, syndromes, ancillary diseaese(s), ailments, or the like associated with one or more diseases or syndromes, or conditions associated with defective insulin metabolism, or defective carbohydrate metabolism, e.g. defective glucose metabolism, including but not limited to type 1 and type 2 diabetes. Examples of complications would include ketoacidosis, coma, retinopathy, diabetc microangiopathy, atherosclerosis, myocardial infarction, stroke, gangrene, hypertriglyceridemia, hypercholesterolemia, cardiomyopathy, dermopathy, diabetic foot syndrome, nephropathy, urinary tract infection, papillary necrosis, cataracts, diabetic gastroenteropathy, constipation, and peripheral vascular disease.

"Conservative substitution" or "conservative amino acid substitution" refers to a replacement of one or more amino acid residue(s) in a protein or peptide as exemplified in Table 1.

"Fragment thereof" refers to a fragment, piece, or sub-region of a peptide, or a nucleic acid, such that the fragment comprises 2 (two) or more contiguous amino acids, or alternatively about 5 to 14 amino acids, or greater; or 10 or more nucleotides that are contiguous in the parent peptide or nucleic acid molecule. Fragment thereof may or may not retain biological activity. For example, a fragment of a peptide disclosed herein could be used as an antigen to raise a specific antibody against the parent peptide from which the fragment is derived. When referring to a nucleic acid molecule, "fragment thereof" refers to 10 or more contiguous nucleotides, derived from the parent nucleic acid, and also, owing to the genetic code, to the complementary sequence. For example if the fragment entails the sequence 5'-AGCTAG-3', then "fragment thereof" would also include the complementary sequence, 3'-TCGATC-5'.

The term "fusion protein" denotes a hybrid protein molecule not found in nature comprising a translational fusion or enzymatic fusion in which two or more different proteins or fragments thereof are covalently linked on a single polypeptide chain.

"Fusion partner" refers to a sequence of amino acids in a BLT fusion protein wherein said sequence does not derive from BLT, e.g. the sequence identified herein as SEQ ID NO:6.

"Functional fragment" or "functionally equivalent fragment", as used herein, refers to a region, or fragment of a full length BLT that retains biological activity, i.e. the ability to enhance the effect of insulin in vivo and/or in vitro; and/or the ability to promote a lowering of blood glucose in vivo, or to enhance glucose uptake into a cell or tissue in vitro. Functional fragments may also provide the biological activity manifested by a full length BLT, in vivo and/or in vitro, viz. the capacity to promote glucose uptake and/or to enhance the effects of insulin and/or to enhance insulin sensitivity. Functional fragments may be produced by cloning technology, or by chemical synthetic means or by chemical or enzymatic cleavage.

"Host cell" refers to any eucaryotic or procaryotic cell that is suitable for propagating and/or expressing a cloned gene contained on a vector that is introduced into said host cell by, for example, transformation or transfection, or the like.

The term "homolog" or "homologous" describes the relationship between different nucleic acid molecules or amino acid sequences in which said sequences or molecules are related by identity or partial identity and/or similarity at one or more blocks or regions of sequence within said molecules.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of homology, the stringency of hybridization, and the length of hybridizing strands.

The term "insulinotropic" refers to an insulin enhancing activity, for example, by reversing or relieving the effects of insulin insensitivity.

"Isolated nucleic acid compound" refers to any RNA or DNA sequence, however constructed or synthesized, which is locationally distinct from its natural location, e.g. in a cell.

A "nucleic acid probe" or "probe" as used herein is a labeled nucleic acid compound which hybridizes with another nucleic acid compound. "Nucleic acid probe" means a single stranded nucleic acid sequence that will combine with a complementary or partially complementary single stranded target nucleic acid sequence to form a double-stranded molecule. A nucleic acid probe may be an oligonucleotide or a nucleotide polymer. A probe will usually contain a detectable moiety which may be attached to the end(s) of the probe or be internal to the sequence of the probe.

The term "plasmid" refers to an extrachromosomal genetic element. The plasmids disclosed herein are commercially available, publicly available on an unrestricted basis, or can be constructed from readily available plasmids in accordance with published procedures.

A "primer" is a nucleic acid fragment which functions as an initiating substrate for enzymatic or synthetic elongation of, for example, a nucleic acid molecule.

The term "promoter" refers to a nucleic acid sequence that directs transcription, for example, of DNA to RNA. An inducible promoter is one that is regulatable by environmental signals, such as carbon source, heat, or metal ions, for example. A constitutive promoter generally operates at a constant level and is not regulatable.

The terms "protein" and "peptide" are used interchangeably throughout, referring to two or more amino acid residues covalently linked by peptide bonding. In some instances these terms describe amino acid biopolymers comprising greater than 10 and up to about 500 amino acid residues linked by peptide bonding.

"Recombinant DNA cloning vector" as used herein refers to any autonomously replicating agent, including, but not limited to, plasmids and phages, comprising a DNA molecule to which one or more additional DNA segments can or have been incorporated.

The term "recombinant DNA expression vector" or "expression vector" as used herein refers to any recombinant DNA cloning vector, for example a plasmid or phage, in which a promoter and other regulatory elements are present thereby enabling transcription of an inserted DNA, which may encode a protein.

The term "stringency" refers to hybridization conditions. High stringency conditions disfavor non-homologous base-pairing. Low stringency conditions have the opposite effect. Stringency may be altered, for example, by temperature and salt concentration.

"Low stringency" conditions comprise, for example, a temperature of about 37° C. or less, a formamide concentration of less than about 50%, and a moderate to low salt (SSC) concentration; or, alternatively, a temperature of about 50° C. or less, and a moderate to high salt (SSPE) concentration, for example 1M NaCl.

"High stringency" conditions comprise, for example, a temperature of about 42° C. or less, a formamide concentration of less than about 20%, and a low salt (SSC) concentration; or, alternatively, a temperature of about 65° C., or less, and a low salt (SSPE) concentration. For example, high stringency conditions comprise hybridization in 0.5 M NaHPO$_4$, 7% sodium dodecyl sulfate (SDS), 1 mM EDTA at 65° C. (Ausubel, F. M. et al. *Current Protocols in Molecular Biology*, Vol. I, 1989; Green Inc. New York, at 2.10.3).

"SSC" comprises a hybridization and wash solution. A stock 20×SSC solution contains 3M sodium chloride, 0.3M sodium citrate, pH 7.0.

"SSPE" comprises a hybridization and wash solution. A 1×SSPE solution contains 180 mM NaCl, 9 mM Na$_2$HPO$_4$, 0.9 mM NaH$_2$PO$_4$ and 1 mM EDTA, pH 7.4.

"Substantially pure" in reference to a protein means that said protein is separated from other cellular and non-cellular components, including other protein molecules. A substantially pure preparation is at least 85% pure; and preferably about at least 95% pure. A "substantially pure" protein could be prepared by any number of suitable methods including, for example, the IMAC protein purification method (U.S. Pat. No. 4,569,794) herein incorporated by reference.

"Treating" as used herein describes the management and care of a patient for the purpose of combating a disease, condition, or disorder and includes the administration of a protein of the present invention to prevent the onset of the symptoms or complications, alleviating the symptoms or complications, or eliminating the disease, condition, or disorder.

All references cited in this specification are herein incorporated by reference.

Beta-lipotropin was isolated in 1964 from ovine pituitary glands, and its primary structure reported the following year (Li et. al. *Nature*, 208, 1093, 1965). Since then the primary sequence of sheep, bovine, ovine, mouse, porcine, guinea pig, rat, elephant, and human BLTs have been reported. (See e.g. Lohmar and Li, *Biochim. Biophys. Acta*, 147, 381, 1967; Li and Chung, *Nature*, 260, 622, 1976; Drouin and Goodman, *Nature*, 288, 619, 1980; Li et al. *Int. J. Pept. Prot. Res.* 32, 573–78, 1988; Blake and Li, *Proc. Nat. Acad. Sci.* 80, 1556–1559, 1983; Takahashi et.al. *FEBS Lett.* 135, 97–102, 1981; all of which are herein incorporated by reference). The sequence data reveal that the carboxy terminus of BLT is highly conserved across species. On the other hand, considerable sequence differences occur at the amino terminal end of BLT molecules from different species.

The present invention relates further to BLT fusion proteins, comprising human BLT (SEQ ID NO:8), or BLT from another species, or a functional fragment thereof. Exemplary BLT fusion proteins are disclosed herein as SEQ ID NO:2, SEQ ID NO:5, and SEQ ID NO:7.

Functional fragments of BLT are conveniently identified as fragments of BLT that exhibit biological activity, for example, the capacity to ameliorate diabetic symptoms when administered to a mammal in need thereof, or to diminish serum insulin levels, and/or enhance insulin sensitivity, and/or lower blood glucose levels, and/or stimulate glucose uptake in adipose or muscle tissue, in vivo or in vitro, or in adipocytes in vitro. Functional fragments of BLT comprise any fragment that retains biological activity and that comprises at least two (2) or more amino acid residues that are in some instances contiguous in the BLT protein. Preferred fragments comprise a contiguous region of BLT mapping partly or wholly outside the region of residues 59 through 89 of human BLT (SEQ ID NO:8), or equivalent region of non-human BLT (i.e. region encoding β-endorphin)

Exemplary functional fragments of human BLT are disclosed herein as SEQ ID NO:9 through SEQ ID NO:25. Preferred fragments are designated herein as SEQ ID NO:9 through SEQ ID NO:13; most preferred fragments are designated herein as SEQ ID NO:10, SEQ ID NO:12, and SEQ ID NO:13. In some instances, a functional fragment may comprise an internal deletion of the parent BLT, e.g. SEQ ID NO:13, in which amino acid residues 7 through 23 of human BLT are deleted. Functional fragments may be produced by solid phase chemical synthesis and/or by recombinant DNA techniques well known to the skilled artisan. See e.g. K. Struhl, "Reverse biochemistry: Methods and applications for synthesizing yeast proteins in vitro," *Meth. Enzymol.* 194, 520–535. For example, in one method, a nested set of deletion mutations are introduced into a nucleic acid encoding BLT such that varying amounts of the peptide coding region are deleted, either from the amino terminal end, or from the carboxyl end of the molecule. This method can also be used to create internal fragments of the intact protein in which both the carboxyl and amino terminal ends are removed. Suitable nucleases for creating such deletions include, for example Bal31, or in the case of a single stranded nucleic acid molecule, mung bean nuclease. For simplicity, it is preferred that the BLT encoding nucleic acid be cloned into a single-stranded cloning vector, such as bacteriophage M13, or equivalent. If desired, the resulting deletion fragments can be subcloned into any suitable vector for propagation and expression in any suitable host cell.

Functional fragments of BLT may be identified and tested for biological activity using any suitable assay, for example, the ability of a peptide fragment to stimulate or enhance insulin sensitivity and/or glucose uptake by cells in vivo or in vitro.

Functional analogs of BLT can be generated by deletion, insertion, inversion, and/or substitution of one or more amino acid residues in said BLT, or any one of the peptides disclosed herein. Substitution analogs can generally be made by solid phase or recombinant techniques in which single or multiple conservative amino acid substitutions are made, for example, according to Table 1. Generally, in the case of multiple substitutions, it is preferred that less than ten residues be changed in any given molecule, most preferably between one to five residues are changed in any given molecule such that about between 90% to 99% of residues are identical with the sequence of SEQ ID NO:8; alternatively, such that about between 95% to 99% of residues are identical with SEQ ID NO:8 or other suitable BLT from another species.

For example, analogs of human BLT (SEQ ID NO:8) comprising single or multiple amino acid substitutions in the region between amino acid residues 1 through 89, comprise substitutions wherein:

the residue at position 1 is alternatively Glu, Ala, Asp or Gln;

the residue at position 2 is alternatively Leu, Ile, Val, or Met;

the residue at position 3 is alternatively Thr, Ala, Glu, Ser, Pro, or Gly;

the residue at position 4 is alternatively Gly, Arg, Ala, Leu, Pro, or Ser;

the residue at position 5 is alternatively Glu, Gln, Asp, Asn, or Ala;

the residue at position 6 is alternatively Arg, Glu, Leu, Lys, Gln, or Ala;

the residue at position 7 is alternatively Leu, Pro, Asp, Val, Ile, or Met;

the residue at position 8 is alternatively Arg, Glu, Ala, Tyr, Leu, Lys, Pro, Gln or Trp;

the residue at position 9 is alternatively Glu, Ala, Pro, Asp, Asn, or Gln;

the residue at position 10 is alternatively Gly, Ala, Ser, or Asp;

the residue at position 11 is alternatively Asp, Arg, Pro, Asn, Gln, Ala, or Glu;

the residue at position 12 is alternatively Gly, Ala, Ser, or Met;

the residue at position 13 is alternatively Pro, Glu, Gly, or Val;

the residue at position 14 is alternatively Asp, Glu, Asn, Gln, or Gly;

the residue at position 15 is alternatively Gly, Ala, Ser, or Glu;

the residue at position 16 is alternatively Pro, Gln, Leu, Gly, or Glu;

the residue at position 17 is alternatively Ala, Asp, Ser, or Gly;

the residue at position 18 is alternatively Asp, Glu, Gln, or Asn;

the residue at position 19 is alternatively Asp, Glu, Asn, or Gln;

the residue at position 20 is alternatively Gly, Ser, or Ala;

the residue at position 21 is alternatively Ala, Gly, Ser, or Phe;

the residue at position 22 is alternatively Gly, Ala, Ser, or Lys;

the residue at position 23 is alternatively Ala, Phe, Thr, Gly, Ser, or Leu;

the residue at position 24 is alternatively Gln, Arg, Asp, Asn, Leu, or Val;

the residue at position 25 is alternatively Ala, Leu, Asp, Ile, Gly, Ser, or Thr;

the residue at position 26 is alternatively Asp, Glu, Gly, Asn, Gln, or Lys;

the residue at position 27 is alternatively Leu, Ala, Ile, Met, or Val;

the residue at position 28 is alternatively Glu, Gln, Asn, or Asp;

the residue at position 29 is alternatively His, Asn, Tyr, Ala, Gln or Glu;

the residue at position 30 is alternatively Ser, Gly, Glu, Ala, Leu, or Asp;

the residue at position 31 is alternatively Leu, Ala, Val, Met, or Ile;

the residue at position 32 is alternatively Leu, Ala, Val, Ile, Met, or Pro;

the residue at position 33 is alternatively Val, Ala, Glu, Leu, Ile, Met, or Arg;

the residue at position 34 is alternatively Ala, Ser, Pro, Glu, or Gly;

the residue at position 35 is alternatively Ala, Asp, Gly, Ser, or Leu;

the residue at position 36 is alternatively Glu, Ala, Thr, Leu, Asp, Asn, or Gln;

the residue at position 37 is alternatively Lys, Glu, Thr, Arg, Gln, or Asp;

the residue at position 38 is alternatively Lys, Arg, Gin, or Glu;

the residue at position 39 is alternatively Asp, Ala, Asn, Glu, Gln, or Lys;

the residue at position 40 is alternatively Glu, Ser, Asp, Asn, Gln, or Gly;

the residue at position 41 is alternatively Gly, Ala, or Ser;

the residue at position 42 is alternatively Pro, Gly, Ser, or Asn;

the residue at position 43 is alternatively Tyr, Phe, or Trp;

the residue at position 44 is alternatively Arg, Lys, Gln, or Glu;

the residue at position 45 is alternatively Met, Ile, Ser, or Val;

the residue at position 46 is alternatively Glu, Gln, Asp, Asn, His, Arg or Gly;

the residue at position 48 is alternatively Tyr or Trp;

the residue at position 49 is alternatively Arg or Lys;

the residue at position 50 is alternatively Trp, Tyr, or Phe;

the residue at position 51 is alternatively Gly, Ala, Ser, or gln;

the residue at position 52 is alternatively Ser, Thr, Asn, or Ala;

the residue at position 53 is alternatively Pro or Gly;

the residue at position 54 is alternatively Pro, Ala, Gly, Arg, Leu, or Thr;

the residue at position 55 is alternatively Lys, Arg, Gln, or Ala;

the residue at position 56 is alternatively Asp, Asn, Glu, Gln, Ala, Gly, or Ile;

the residue at position 57 is alternatively Lys, Gln, or Arg;

the residue at position 58 is alternatively Arg, Gln, or Lys;

the residue at position 59 is alternatively Tyr, Phe or Trp;

the residue at position 60 is alternatively Gly, Ala, or Ser;

the residue at position 61 is alternatively Gly, Ala, or Ser;

the residue at position 62 is alternatively Phe, Tyr, or Trp;

the residue at position 63 is alternatively Met, Leu, Ile, or Val;

the residue at position 64 is alternatively Thr, Ala, Ser, or Lys;

the residue at position 65 is alternatively Ser, Ala, Thr, or Pro;

the residue at position 66 is alternatively Glu, Asp, Asn, Lys, or Gln;

the residue at position 67 is alternatively Lys, Arg, or Gln;

the residue at position 68 is alternatively Ser, Ala, Thr, or Gly;

the residue at position 69 is alternatively Gln, Glu, Asp, Asn, Arg, or His;

the residue at position 70 is alternatively Thr, Ser, Ala, or Lys;

the residue at position 71 is alternatively Pro or Gly;

the residue at position 72 is alternatively Leu, Ile, Met, or Val;

the residue at position 73 is alternatively Val, Leu, Ile, or Met;

the residue at position 74 is alternatively Thr, Ala, or Ser;

the residue at position 75 is alternatively Leu, Ile, Met, or Val;

the residue at position 76 is alternatively Phe, Tyr, Trp, or Leu;

the residue at position 77 is alternatively Lys, Gln, or Arg;

the residue at position 78 is alternatively Asn, Asp, Glu, Gln, or His;

the residue at position 79 is alternatively Ala, Gly, Ser, Ile or Val;

the residue at position 80 is alternatively Ile, Leu, Met, Val, or Thr;

the residue at position 81 is alternatively Ile, Met, Val, Thr, or Leu;

the residue at position 82 is alternatively Lys, Gln, or Arg;

the residue at position 83 is alternatively Asn, Asp, Glu, Gln, or Ser;

the residue at position 84 is alternatively Ala, Val, Ser, Gly, or Glu;

the residue at position 85 is alternatively Tyr, Phe, Trp, or His;

the residue at position 86 is alternatively Lys, Gln, or Arg;

the residue at position 87 is alternatively Lys, Gln, or Arg;

the residue at position 88 is alternatively Gly, Ala, or Ser;

the residue at position 89 is alternatively Glu, Gln, Asp, Asn, or His.

Additional specific substitutions in human BLT (SEQ ID NO:8) include single or multiple substitutions in SEQ ID NO:8, wherein:

the residue at position 3 is Glu;

the residue at position 4 is Arg;

the residue at position 6 is Gln;

the residue at position 7 is Pro;

the residue at position 8 is Glu, Ala, or Pro;

the residue at position 9 is Pro or Ala ;

the residue at position 11 is Arg or Pro;

the residue at position 16 is Leu or Gln;

the residue at position 21 is Phe;

the residue at position 23 is Thr, Leu or Pro;

the residue at position 24 is Arg or Val;

the residue at position 27 is Ala;

the residue at position 29 is Asn, Tyr, or Ala;

the residue at position 30 is Glu;

the residue at position 31 is Ala;

the residue at position 32 is Ala;

the residue at position 33 is Ala or Glu;

the residue at position 34 is Pro or Ser;

the residue at position 35 is Asp;

the residue at position 36 is Thr or Ala;

the residue at position 37 is Glu;

the residue at position 40 is Ser;

the residue at position 42 is Ser;

the residue at position 44 is Glu;

the residue at position 45 is Val;

the residue at position 52 is Asn;

the residue at position 54 is Ala or Arg;

the residue at position 56 is Gly;

the residue at position 84 is Val;

the residue at position 85 is His; and the residue at position 89 is His.

TABLE 1

Exemplary Amino Acid Substitutability

| ORIGINAL RESIDUE | EXEMPLARY SUBSTITUTIONS |
| --- | --- |
| ALA | SER, GLY |
| ARG | LYS |
| ASN | GLN, HIS, ASP, GLU |
| ASP | GLU, GLN, ASN |
| CYS | SER |
| GLN | ASN, GLU, ASP |
| GLU | ASP, GLN, ASN |
| GLY | PRO, SER, ALA |
| HIS | ASN, GLN |
| ILE | LEU, VAL, MET |
| LEU | ILE, VAL, MET |
| LYS | ARG, GLN, GLU |
| MET | LEU, ILE, VAL |
| PHE | MET, LEU, TYR, TRP |
| SER | THR, ALA |
| THR | SER, ALA |
| TRP | TYR, PHE |
| TYR | TRP, PHE |
| VAL | ILE, LEU, MET |
| PRO | GLY |

TABLE 2

SEQUENCE LISTING IDENTIFIER

| SEQ ID NO: | DESCRIPTION |
| --- | --- |
| 1 | Nucleic acid encoding Met-Arg-BLT |
| 2 | Amino acid sequence of Met-Arg-BLT |
| 3 | Amino acid sequence of a fusion partner used to create SEQ ID NO:5 |
| 4 | Oligonucleotide linker used in constructing BLT fusion |
| 5 | Amino acid sequence of a BLT fusion |
| 6 | Glutathione-S-transferase (GST) fusion partner |
| 7 | GST/BLT fusion protein |
| 8 | Amino acid sequence of Human BLT |
| 9 | Human BLT (1–49) |
| 10 | Human BLT (50–89) |
| 11 | Human BLT (38–67) |
| 12 | Human BLT (38–89) |
| 13 | Human BLT (Δ7–23) |
| 14 | Human BLT (1–14) |
| 15 | Human BLT (8–21) |
| 16 | Human BLT (15–28) |
| 17 | Human BLT (22–35) |
| 18 | Human BLT (29–42) |
| 19 | Human BLT (36–49) |
| 20 | Human BLT (43–56) |
| 21 | Human BLT (50–63) |
| 22 | Human BLT (57–70) |
| 23 | Human BLT (64–77) |
| 24 | Human BLT (71–84) |
| 25 | Human BLT (78–89) |
| 26 | BLT analog (1:Glu–Ala) |
| 27 | BLT analog (3:Thr–Ser) |
| 28 | BLT analog (5:Gln–Glu) |
| 29 | BLT analog (7:Leu–Asp) |
| 30 | BLT analog (10:Gly–Ala) |
| 31 | BLT analog (15:Gly–Glu) |
| 32 | BLT analog (17:Ala–Gly) |
| 33 | BLT analog (23:Ala–Phe) |
| 34 | BLT analog (30:Ser–Glu) |
| 35 | BLT analog (42:Pro–Ser) |

Gene Isolation Procedures

Those skilled in the art will recognize that a nucleic acid encoding BLT, or a BLT fusion, can be obtained by a plurality of recombinant DNA techniques including, for example, polymerase chain reaction (PCR) amplification, or de novo DNA synthesis. (See e.g., T. Maniatis et al. *Molecular Cloning: A Laboratory Manual*, 2d Ed. Chap. 14 (1989)).

For example, oligonucleotide primers targeted to the 3' and 5' ends of SEQ ID NO:1 can be used for PCR amplification of Met-Arg-BLT. See e.g. *PCR Protocols: A Guide to Method and Application*, Ed. M. Innis et al., Academic Press (1990). A PCR amplification comprises template DNA, suitable enzymes, primers, and buffers, and is conveniently carried out in a DNA Thermal Cycler (Perkin Elmer Cetus, Norwalk, Conn.). A positive result is determined by detecting an appropriately-sized DNA fragment (viz. 273 base pairs) following agarose gel electrophoresis.

Protein Production Methods

One embodiment of the present invention relates to the use of BLT protein as a pharmaceutical compound.

Skilled artisans will recognize that the proteins and fragments, or functional fragments thereof, of the present invention can be synthesized by a number of different methods, such as chemical methods well known in the art, including solid phase peptide synthesis or recombinant methods. Both methods are described in U.S. Pat. No. 4,617,149, incorporated herein by reference.

The principles of solid phase chemical synthesis of proteins are well known in the art and may be found in general texts in the area. See, e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celsius or below, preferably −20° C. for thirty minutes followed by thirty minutes at 0° C.

In general, the synthesis of a peptide consists of a series of steps as follows. First, an amino acid with its α-amino (and side chain functional group if necessary) protected is activated to form a reactive ester. This activated amino acid is attached to an inert solid support through this activated ester group and the bound amino acid is thoroughly washed. Following this step, a second protected amino acid is activated to an ester in a separate reaction. The α-amino group of the first amino acid is de-protected yielding a reactive amine, and the second activated amino acid is reacted with it to form a di-peptide on the solid support. Sequential repetition of these steps results in a peptide of increasing length. Following completion of the synthesis, the peptide is removed from the solid support and the side chain functional groups are de-protected by treatment of the peptide with a strong acid. The peptide is then separated from the solid support by filtration, precipitated with an organic solvent, and purified by a variety of techniques well known in the art.

In the present instance, the α-amino protecting group is the 9-fluoroenylmethylcarbonyl (Fmoc) group. Side chain protecting groups are; Boc (for Lys and Trp residues), Trt (for Asn, His, Gln), tBu (for Ser, Thr, Tyr), OtBu (for Asp, Glu) and Pmc (for Arg). Active esters are formed with 2-(1H-benzo-triazole-1-yl)-1,1,3,3-tetramethyl uronium hexafluorophosphate (HBTU).

The α-amino Fmoc protecting group is removed by treatment of the solid phase with piperidine. Under these conditions the Fmoc group is readily removed while the solid phase linkage and side chain protecting groups are not effected. The protected amino acid to be added to a nascent peptide chain is activated with HBTU.

The synthesis of human BLT presented several special challenges. First, the sequence of the peptide contains a ser-pro-pro tripeptide segment. Standard coupling chemistry results in a series of deletion errors in the synthesis. Such deletions are minimized by double-coupling the pro residues. In the preferred embodiment the synthesis is carried out by double-coupling the Pro and Ser residues. In addition, after completion of the coupling step, any remaining unreacted, deprotected peptide is blocked with acetic anhydride to prevent chain lengthening of a deletion peptide.

Second, the human peptide contains 3 asp-gly dipeptide sequences. These sequences are susceptible to cyclic imine formation, even when the asp side chains are protected. These cyclic imines may then react with piperidine in the deprotections step to generate a piperidine-modified peptide. This cyclization was eliminated by utilization of N-a-Hmb protection of each glycine residue preceding an asp residue.

See e.g. Qubbell et.al. *J. Chem. Soc. Chem. Commun.* 2343, 1994, herein incorporated by reference. Two of the asp-gly dipeptides are preceded by a pro. Due to this feature of the sequence, and the lower reactivity of the hmb protected amino acids, each of these are multiply-coupled, and then capped with acetic anhydride. In a preferred embodiment these are double-coupled.

In a preferred method the peptide is synthesized in a single run using Fmoc chemistry. The synthesis of BLT is complicated by the presence of several asp-gly dipeptide sequences in the N-terminal portion of the molecule. Aspartyl side chains in asp-gly didpeptide sequences have been observed to undergo base catalyzed cyclization and subsequent addition with piperidine during FMOC synthesis. This reaction is eliminated by use of Fmoc-(FmocHmb)-glycine at each asp-gly sequence in the synthesis. Protection of the glycyl amide with the Hmb group inhibits the cyclization of the aspartyl side chain. Following cleavage, deprotection, and reverse phase HPLC purification, the peptide can be analyzed by electospray mass spectometry. The major species seen in this synthesis of BLT is the full length peptide having the expected mass. Use of this method allows production of quantities of purified protein in excess of 100 mg from a single run at the 0.1 mmole scale.

The proteins of the present invention can also be produced by recombinant DNA methods. Expression of a cloned nucleic acid encoding BLT, or BLT fusion (e.g. SEQ ID NO:1), can be carried out in a variety of suitable host cells, well known to those skilled in the art. For this purpose, a BLT encoding nucleic acid is introduced into a host cell by any suitable means, well known to those skilled in the art. While chromosomal integration is within the scope of the present invention, it is preferred that the sequence be cloned into a suitable extra-chromosomally maintained expression vector so that the coding region of the BLT gene is operably-linked to a constitutive or inducible promoter.

The basic steps in the recombinant production of the BLT protein are:

a) constructing a natural, synthetic or semi-synthetic DNA encoding BLT, or a fusion protein thereof;

b) integrating said DNA into an expression vector in a manner suitable for expressing said protein;

c) transforming or otherwise introducing said vector into an appropriate eucaryotic or prokaryotic host cell forming a recombinant host cell, d) culturing said recombinant host cell in a manner amenable to expression of said protein; and e) recovering and substantially purifying said protein by any suitable means.

Expressing Recombinant BLT Fusion Protein in Procaryotic and Eucaryotic Host Cells Human beta-lipotropin (BLT) is an 89-amino acid hormone that is produced by the pituitary in the form of a precursor protein that undergoes post-translational processing to generate several bioactive hormones including BLT. Because BLT is small and contains proteolytically sensitive sites, we have produced this protein initially by chemical synthesis. However, this method is not useful for generating large quantities. In this invention, we describe a method by which BLT can be produced in bacterial or fungal expression hosts in the form of fusion proteins. These fusion proteins are protected from proteolytic degradation and allow for recovery of intact BLT by methods described below.

In *E. coli*, BLT is produced as a fusion protein which can be recovered from cell lysates in the presence of high salt by conventional purification methods. The fusion protein contains a recognition site for specific proteases which are used to separate the fusion partner from BLT. In *Pichia pastoris*, the fusion protein is cleaved upon secretion from the cell in such a way that native BLT can be detected and recovered intact from the culture medium.

This method offers a production process for BLT. Unlike chemical synthesis, the process described herein can be scaled up to produce large amounts of BLT.

Procaryotes may be employed in the production of recombinant BLT protein. For example, the *Escherichia coli* K12 strain 294 (ATCC No. 31446) is particularly useful for expression of foreign proteins in a procaryotic cell. Other strains of *E. coli*, bacilli such as *Bacillus subtilis*, enterobacteriaceae such as *Salmonella typhimurium* or *Serratia marcescans*, various Pseudomonas species and other bacteria, such as Streptomyces, may also be employed as host cells in the cloning and expression of the recombinant proteins of this invention.

Promoter sequences suitable for driving the expression of genes in procaryotes include b-lactamase [e.g. vector pGX2907, ATCC 39344, contains a replicon and b-lactamase gene], lactose systems [Chang et al., *Nature* (London), 275:615 (1978); Goeddel et al., *Nature* (London), 281:544 (1979)], alkaline phosphatase, and the tryptophan (trp) promoter system [vector pATH1 (ATCC 37695)], which is designed to facilitate expression of an open reading frame as a trpE fusion protein under the control of the trp promoter. Hybrid promoters such as the tac promoter (isolatable from plasmid pDR540, ATCC-37282) are also suitable, as are T7 promoters. Still other bacterial promoters, whose nucleotide sequences are generally known, may be ligated to DNA encoding the protein of the instant invention, using linkers or adapters to supply any required restriction sites. Promoters for use in bacterial systems also will contain a Shine-Dalgarno sequence operably-linked to the DNA encoding the desired polypeptides. These examples are illustrative rather than limiting.

The proteins of this invention may be synthesized either by direct expression or as a fusion protein from which the fusion partner may be removed by enzymatic or chemical cleavage. In principle, this invention applies to any fusion system that can be expressed in bacterial or fungal hosts. In one embodiment of a suitable fusion system, a recognition site is placed between BLT and a fusion partner, wherein, for example, the fusion partner is placed at the amino terminal end of BLT. A suitable site can be a recognition sequence for a protease, or a site that is susceptible to chemical cleavage.

Examples of suitable bacterial fusion partners include glutathione-S-transferase, maltose binding protein, procarboxypeptidase, calmodulin binding protein or any amino-terminally located sequence that promotes high-level expression of a fusion protein.

Examples of suitable proteases include factor Xa, thrombin and enterokinase. Agents for chemical cleavage include cyanogen bromide, acid, etc.

Examples of fusion partners that are useful in fungal systems include the alpha mating factor, propeptide, human serum albumin and any other sequence that promotes expression and secretion of the fusion protein and subsequent cleavage (during secretion) to release native BLT into the culture medium.

In one approach, a BLT fusion protein comprises a native BLT sequence fused to a dipeptide (viz. Met-Arg) at the amino terminal end of the native BLT molecule (e.g. SEQ ID NO:2). The dipeptide partner of this fusion molecule can be released by treatment with Cathepsin C, and the native BLT molecule purified by techniques known in the art, such as, for example, HPLC. In another method for producing recombinant BLT fusion protein, glutathione-S-transferase (GST) is used as the fusion partner to produce the protein designated herein as SEQ ID NO:7, essentially as described in Smith and Johnson (*Gene*, 67, 31, 1988), hereby incorporated by reference.

It is often observed in the production of certain peptides in recombinant systems that expression as a fusion protein prolongs the lifespan, increases the yield of the desired peptide, or provides a convenient means of purifying the protein. This is particularly relevant when expressing mammalian proteins in procaryotic hosts. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to procaryotes, a variety of amphibian expression systems such as frog oocytes, and mammalian cell systems can be used. The choice of a particular host cell depends to some extent on the particular expression vector used. Exemplary mammalian host cells suitable for use in the present invention include HepG-2 (ATCC HB 8065), CV-1 (ATCC CCL 70), LC-MK$_2$ (ATCC CCL 7.1), 3T3 (ATCC CCL 92), CHO-K1 (ATCC CCL 61), HeLa (ATCC CCL 2), RPMI8226 (ATCC CCL 155), H4IIEC3 (ATCC CCL 1600), C127I (ATCC CCL 1616), HS-Sultan (ATCC CCL 1484), and BHK-21 (ATCC CCL 10), for example.

A wide variety of vectors are suitable for transforming mammalian host cells. For example, the pSV2-type vectors comprise segments of the simian virus 40 (SV40) genome required for transcription and polyadenylation. A large number of plasmid pSV2-type vectors have been constructed, such as pSV2-gpt, pSV2-neo, pSV2-dhfr, pSV2-hyg, and pSV2-b-globin, in which the SV40 promoter drives transcription of an inserted gene. These vectors are widely available from sources such as the American Type Culture Collection (ATCC), 12301 Parklawn Drive, Rockville, Md., 20852, or the Northern Regional Research Laboratory (NRRL), 1815 N. University Street, Peoria, Ill., 61604.

Promoters suitable for expression in mammalian cells include the SV40 late promoter, promoters from eukaryotic genes, such as, for example, the estrogen-inducible chicken ovalbumin gene, the interferon genes, the glucocorticoid-inducible tyrosine aminotransferase gene, the thymidine kinase gene promoter, and the promoters of the major early and late adenovirus genes.

Transfection of mammalian cells with vectors can be performed by a plurality of well known processes including, but not limited to, protoplast fusion, calcium phosphate co-precipitation, electroporation and the like. See, e.g., Maniatis et al., supra.

Some viruses also make appropriate vectors. Examples include the adenoviruses, the adeno-associated viruses, the vaccinia virus, the herpes viruses, the baculoviruses, and the rous sarcoma virus, as described in U.S. Pat. No. 4,775,624, incorporated herein by reference.

Eucaryotic microorganisms such as yeast and other fungi are also suitable host cells. The yeasts *Saccharomyces cerevisiae* and *Pichia pastoris* are the preferred eucaryotic microorganisms. Other yeasts such as *Kluyveromyces lactis* are also suitable. For expression in Saccharomyces, the plasmid YRp7 (ATCC-40053), for example, may be used. See, e.g., L. Stinchcomb et al., *Nature*, 282, 39 (1979); J. Kingsman et al., *Gene*, 7, 141 (1979); S. Tschemper et al., *Gene*, 10, 157 (1980). Plasmid YRp7 contains the TRP1 gene which provides a selectable marker for use in a trp1 auxotrophic mutant.

Other embodiments of the present invention comprise isolated nucleic acid sequences that encode BLT, or fragment thereof. As skilled artisans will recognize, the amino acid compounds of the invention can be encoded by a multitude of different nucleic acid sequences. Because these alternative nucleic acid sequences would encode the same amino acid sequences, the present invention further comprises these alternate nucleic acid sequences.

The BLT encoding nucleic acids of the invention may also be produced by chemical synthetic methods. The synthesis of nucleic acids is well known in the art. See, e.g., E. L. Brown, R. Belagaje, M. J. Ryan, and H. G. Khorana, *Methods in Enzymology*, 68:109–151 (1979). Fragments of the DNA sequence corresponding to BLT could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) using phosphoramidite chemistry, thereafter ligating the fragments so as to reconstitute the entire gene. Alternatively, phosphotriester chemistry may be employed to synthesize the nucleic acids of this invention. (See, e.g., M. J. Gait, ed., *Oligonucleotide Synthesis, A Practical Approach*, (1984)).

Vectors

Another aspect of the present invention relates to recombinant DNA cloning vectors and expression vectors comprising the nucleic acids of the present invention. The preferred nucleic acid vectors are those which comprise DNA.

The most preferred recombinant DNA vectors comprise the isolated DNA sequence, SEQ ID NO:1.

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene desired in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. The practitioner also understands that the amount of nucleic acid or protein to be produced dictates, in part, the selection of the expression system. Regarding promoter sequences, inducible promoters are preferred because they enable high level, regulatable expression of an operably-linked gene. The skilled artisan will recognize a number of suitable promoters that respond to a variety of inducers, for example, carbon source, metal ions, and heat. Other relevant considerations regarding an expression vector include whether to include sequences for directing the localization of a recombinant protein. For example, a sequence encoding a signal peptide preceding the coding region of a gene is useful for directing the extra-cellular export of a resulting polypeptide.

The present invention also provides a method for constructing a recombinant host cell capable of expressing BLT proteins, said method comprising transforming or otherwise introducing into a host cell a recombinant DNA vector that comprises an isolated DNA sequence that encodes BLT. The preferred host cell is any cell that can accomodate high level expression of an exogenously introduced gene or protein. Transformed host cells may be cultured under conditions well known to skilled artisans such that recombinant BLT is expressed.

The present invention also provides methods for treating humans and other mammals afflicted with diseases or conditions associated with defects in insulin metabolism or carbohydrate metabolism, such as, for example, hyperglycemia, hyperinsulinemia, type 1 and type 2 diabetes, and complications associated therewith. The method comprises administering to an organism in need thereof an effective amount of BLT protein or peptide, or fusion protein comprising BLT, or functional fragment thereof, or analog thereof in a dose between about 1 and 1000 ug/kg body weight. In practicing this method, BLT can be administered in a single daily dose, in multiple doses per day, or by continuous or discontinuous administration via a mechanical pump device that is implanted in the body or attached otherwise thereto. The amount of BLT or related protein or peptide to be administered will be determined by the physician, and depend on such factors as the nature and severity of the condition, syndrome, or disease being treated, and the age and general health of the patient.

The present invention also provides a pharmaceutical composition comprising as the active agent a BLT protein or functional fragment thereof, or analog thereof e.g. that represented by SEQ ID NO:8, or a pharmaceutically acceptable non-toxic salt thereof, in admixture with a pharmaceutically acceptable solid or liquid carrier. The protein, preferably in the form of a pharmaceutically acceptable salt, can be formulated for parenteral administration for the therapeutic or prophylactic treatment of diabetes or complication thereof. For example, compounds of SEQ ID NO:8 or other BLT, or fragment thereof, can be admixed with conventional pharmaceutical carriers and excipients. The compositions comprising BLT protein contain from about 0.1 to 90% by weight of the protein, preferably in a soluble form, and more generally from about 10 to 30%. Furthermore, the present proteins may be administered alone or in combination with other anti-diabetic agents or agents useful in treating diabetes.

For intravenous (IV) use, the BLT protein, fragment, or analog is administered in commonly used intravenous fluid(s) and administered by infusion. Such fluids, for example, physiological saline, Ringer's solution or 5% dextrose solution can be used.

For intramuscular preparations, a sterile formulation, preferably a suitable soluble salt form of the BLT protein, for example SEQ ID NO:8, such as the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

The following examples more fully describe the present invention and the use of BLT to treat diabetes. Those skilled in the art will recognize that the particular reagents, equipment, and procedures described are merely illustrative and are not intended to limit the present invention in any manner.

EXAMPLE 1

Solid Phase Synthesis and Purification of Human BLT Protein

A human BLT peptide (SEQ ID NO:8) was synthesized in a single run using Fmoc chemistry. The synthesis of BLT is complicated by the presence of several asp-gly dipeptide sequences in the N-terminal portion of the peptide. Aspartyl side chains in asp-gly didpeptide sequences have been observed to undergo base catalyzed cyclization and subsequent addition with piperidine during FMOC synthesis. This reaction is eliminated by use of Fmoc-(FmocHmb)-glycine at each asp-gly sequence in the synthesis. Protection of the glycyl amide with the Hmb group inhibits the cyclization of the aspartyl side chain. Following cleavage, deprotection, and reverse phase HPLC purification, the peptide can be analyzed by electrospray mass spectrometry. The major species seen in the synthesis is the full length peptide having the expected mass. Use of this method allows production of quantities of purified protein in excess of 100 mg from a single run at the 0.1 mmole scale.

Materials: Preloaded Fmoc-Glu (OtBu) Wang (1% cross-linked polystyrene functionalized with p-benzoxybenzyl alcohol) resin at approximately 0.6 mmole amino acid/g resin. N-methylpyrrolidone (NMP), piperidine, 2-(1H-benzotriazol-1-yl)-1,1,3,3-tetramethyluronium hexafluorophosphate (HBTU), 2M N,N-Diisopopylethylamine (DIEA) 1-hydroxybenzotriazole (HOBt), Dichloromethane (DCM), Dimethylformamide (DMF).

Resin, preloaded with the Fmoc-protected C-terminal amino acid (0.1 or 0.25 mmole amino acid), was weighed and placed into a reaction chamber. The resin was preswollen by washing with DCM. The resin was then washed with NMP. The N-terminal Fmoc group was removed by incubation of the resin in a 18–22 % solution of piperidine in NMP. Following deprotection, the resin was extensively washed with NMP.

One mmole of the next Fmoc-protected amino acid to be added to the peptide was solubilized in 2.1 g of NMP, 2.0 g of 0.45 M HBTU/HOBt reagent in DMF. Following the solubilization, activation of the amino acid was initiated by addition of 3 ml of 2M DIEA in NMP. The activated amino acid was then added to the deprotected resin and allowed to couple. Upon completion of coupling, the resin was washed extensively with NMP. The complete cycle of deprotection and coupling was then repeated for each successive amino acid.

Specific cycle steps in the synthesis were as follows:

| Cycle | AA | Steps |
|-------|----------|---------------|
| 1 | Glu(OtBu) | Complete wash |
| 2 | Gly | Single Couple |
| 3 | Lys(Boc) | Single Couple |
| 4 | Lys(Boc) | Single Couple |
| 5 | Tyr(tBu) | Single Couple |
| 6 | Ala | Single Couple |

-continued

| Cycle | AA | Steps |
|---|---|---|
| 7 | Asn(Trt) | Single Couple |
| 8 | Lys(Boc) | Single Couple |
| 9 | Ile | Single Couple |
| 10 | Ile | Single Couple |
| 11 | Ala | Single Couple |
| 12 | Asn(Trt) | Single Couple |
| 13 | Lys(Boc) | Single Couple |
| 14 | Phe | Single Couple |
| 15 | Leu | Single Couple |
| 16 | Thr(tBu) | Single Couple |
| 17 | Val | Single Couple |
| 18 | Leu | Single Couple |
| 19 | Pro | Double couple/Ac2O cap |
| 20 | Thr(tBu) | Single Couple |
| 21 | Gln(Trt) | Single Couple |
| 22 | Ser(tBu) | Single Couple |
| 23 | Lys(Boc) | Single Couple |
| 24 | Glu(OtBu) | Single Couple |
| 25 | Ser(tBu) | Single Couple |
| 26 | Thr(tBu) | S.single Couple |
| 27 | Met | Single Couple |
| 28 | Phe | Single Couple |
| 29 | Gly | Single Couple |
| 30 | Gly | Single Couple |
| 31 | Tyr(tBu) | Single Couple |
| 32 | Arg(Pmc) | Single Couple |
| 33 | Lys(Boc) | Single Couple |
| 34 | Asp(OtBu) | Single Couple |
| 35 | Lys(Boc) | Single Couple |
| 36 | Pro | Double couple/Ac2O cap |
| 37 | Pro | Double couple/Ac2O cap |
| 38 | Ser(tBu) | Single Couple |
| 39 | Gly | Single Couple |
| 40 | Trp(Boc) | Single Couple |
| 41 | Arg(Pmc) | Single Couple |
| 42 | Phe | Single Couple |
| 43 | His(Trt) | Single Couple |
| 44 | Glu(OtBu) | Single Couple |
| 45 | Met | Single Couple |
| 46 | Arg(Pmc) | Single Couple |
| 47 | Tyr(tBu) | Single Couple |
| 48 | Pro | Double couple/Ac2O cap |
| 49 | Gly | Single Couple |
| 50 | Glu(OtBu) | Single Couple |
| 51 | Asp(OtBu) | Single Couple |
| 52 | Lys(Boc) | Single Couple |
| 53 | Lys(Boc) | Single Couple |
| 54 | Glu(OtBu) | Single Couple |
| 55 | Ala | Single Couple |
| 56 | Ala | Single Couple |
| 57 | Val | Single Couple |
| 58 | Leu | Single Couple |
| 59 | Leu | Single Couple |
| 60 | Ser(tBu) | Single Couple |
| 61 | His(Trt) | Single Couple |
| 62 | Glu(OtBu) | Single Couple |
| 63 | Leu | Single Couple |
| 64 | Asp(OtBu) | Single Couple |
| 65 | Ala | Single Couple |
| 66 | Gln(Trt) | Single Couple |
| 67 | Ala | Single Couple |
| 68 | Gly | Single Couple |
| 69 | Ala | Single Couple |
| 70 | Gly(Fmoc-hmb) | Double couple/Ac2O cap |
| 71 | Asp(OtBu) | Single Couple |
| 72 | Asp(OtBu) | Single Couple |
| 73 | Ala | Single Couple |
| 74 | Pro | Double couple/Ac2O cap |
| 75 | Gly(Fmoc-hmb) | Double couple/Ac2O cap |
| 76 | Asp(otBu) | Single Couple |
| 77 | Pro | Double couple/Ac2O cap |
| 78 | Gly(Fmoc-hmb) | Double couple/Ac2Ocap |
| 79 | Asp(OtBu) | Single Couple |
| 80 | Gly | Single Couple |
| 81 | Glu(OtBu) | Single Couple |
| 82 | Arg(Pmc) | Single Couple |
| 83 | Leu | Single Couple |
| 84 | Arg(Pmc) | Single Couple |
| 85 | Gln(Trt) | Single Couple |
| 86 | Gly | Single Couple |
| 87 | Thr(tBu) | Single Couple |
| 88 | Leu | Single Couple |
| 89 | Glu(OtBu) | Single Couple |
| 90 | | Final deprotect |

For amino acids that react slowly or inefficiently, 2 separate coupling reactions were performed. Any residual unreacted peptide was blocked by treatment with acetic anhydride. The sequence of steps for one of these amino acids was deprotection, coupling reaction 1, wash, coupling reaction 2, wash, Ac2O cap, wash, deprotection.

Abbreviations: OtBu: t-butyl ester, tBu: t-butyl, Boc: t-butoxycarbonyl, Pmc: 2,2,5,7,8-pentamethylchroma-6-sulfonyl, Hmb: 2-hydroxy-4-methoxybenzyl, Fmoc: 9-fluorenylmethoxycarbonyl.

EXAMPLE 2

Construction of a synthetic gene encoding BLT

Plasmid constructions were performed using standard cloning methodologies as described by Maniatis et.al., Molecular Cloning: A laboratory Manual, Cold Spring Harbor Laboratory, N.Y. (1982). Enzymes and other reagents were obtained from Gibco-BRL, Gaithersburg, Md. or New England Biolabs, Beverly Mass. 01915. Methods for digesting, identifying, recovering and purifying the various oligonucleotides and DNA fragments used in this invention are known to those skilled in the art, as are methods for ligation of these sequences into vectors, transforming host microorganisms, and culturing these host microorganisms under conditions allowing production of plasmid DNA and recombinant protein products.

A DNA sequence encoding human BLT (SEQ ID NO:8) was assembled from 8 chemically synthesized oligonucleotides ranging in size from 52 to 86 bases. The oligonucleotides were generated using a conventional DNA synthesizing apparatus such as the Applied Biosystems model 380A or 380B (commercially available from Applied Biosystems, Inc., 850 Lincoln Center Drive, Foster City, Calif. 94404). The sequence of the oligonucleotides was designed in such a way that 4 of the oligonucleotides generated one strand of the synthetic gene and the remaining 4 oligonucleotides generated the complementary strand of the synthetic gene. Prior to assembly, the oligonucleotides were treated with polynucleotide kinase in the presence of ATP to phosphorylate the free hydroxyl groups of the individual oligonucleotides.

The 8 oligonucleotides were mixed in equimolar concentration (3 picomoles/ul) in a volume of 100 ul, heated to 95° C., and gradually cooled to room temperature over a period of several hours. This allowed for proper base-pairing of the individual oligonucleotides. T4 DNA ligase was added to ligate the oligonucleotides and generate a double-stranded ~285 base-pair DNA, which was analyzed and purified on a 2% agarose gel. This fragment, having "sticky" ends, was ligated into a pUC18 vector digested with NdeI and BamHI. The ligation mix was transformed into competent DH10B cells which were plated onto tryptone-yeast agar plates containing 100 ug/ml of ampicillin. Colonies that grew overnight were analyzed for the presence of plasmids that contained the chemically synthesized gene. This was done by purifying plasmid DNA from these colonies, digesting the plasmid DNA with NdeI and BamHI and verifying the presence of a ~285 base-pair fragment. The correct sequence was subsequently confirmed by DNA sequence analysis. The plasmid was named pOJ838.

EXAMPLE 3

Construction of Plasmids Expressing a BLT Fusion Protein

Because BLT is a small protein, it was advantageous to increase its size by creating a fusion protein. For this purpose, two different fusion partners were used. One was glutathione-S-transferase (GST), having a factor Xa cleavage site and the amino acid sequence designated herein as SEQ ID NO:6, as encoded by vector pGEX-2T (Pharmacia Biotechnology, Piscataway, N.J. 08855); the other was a short peptide sequence MIIGLMVGGVSGSGSGSGD-DDDP (SEQ ID NO:3).

To obtain native beta-lipotropin, fusion proteins are treated either chemically, or by enzymatic digestion, to disassociate beta-lipotropin from its fusion partner. This is accomplished by inserting sites for enzymatic or chemical cleavage between the fusion partner and beta-lipotropin. For GST fusions, recognition sites for enterokinase or factor Xa were chosen; for the small synthetic peptide fusion (SEQ ID NO:3), a proline was inserted, thereby enabling chemical cleavage following acid treatment.

A plasmid encoding a GST fusion with a factor Xa recognition sequence (IEGR) was constructed as follows. Plasmid pOJ838 (pUC18 containing the synthetic beta-lipotropin; See Example 4) was digested with NdeI and NruI, and the largest vector fragment was gel-purified. A synthetic linker of the sequence 5'-TATGAGATCTATCGAAGGTCGTGAGCTCACCGGT-CAGCGTGTTCG-3' (SEQ ID NO:4) and its complement, were mixed in equimolar amounts, heated to 95° C. and allowed to anneal by gradually lowering the temperature to about 25° C. The annealed linker was ligated to the vector fragment, and the ligation mix was transformed into competent DH10B cells. Transformed cells were plated onto tryptone-yeast agar plates containing 100 ug/ml of ampicillin. Colonies that grew overnight were analyzed for the presence of plasmids that contained the linker sequence. This was done by purifying plasmid DNA from these colonies and verifying the presence of a new BglII site that was introduced via the linker. The correct linker sequence was subsequently confirmed by DNA sequence analysis. The resulting plasmid was named pOJ839.

Plasmid pOJ839 was digested with BglII and EcoRI and the small fragment containing the beta-lipotropin gene (now attached to a factor Xa recognition sequence) was gel-purified and ligated into pGEX 2-T digested with BamHI and EcoRI. The ligation mix was transformed into competent DH10B cells, which were plated onto tryptone-yeast agar plates containing 100 ug/ml of ampicillin. Colonies that grew overnight were analyzed for the presence of plasmids that contained a new ~300 bp fragment following digestion with SacI. This new plasmid was named pOJ840.

EXAMPLE 4

Figure 16:
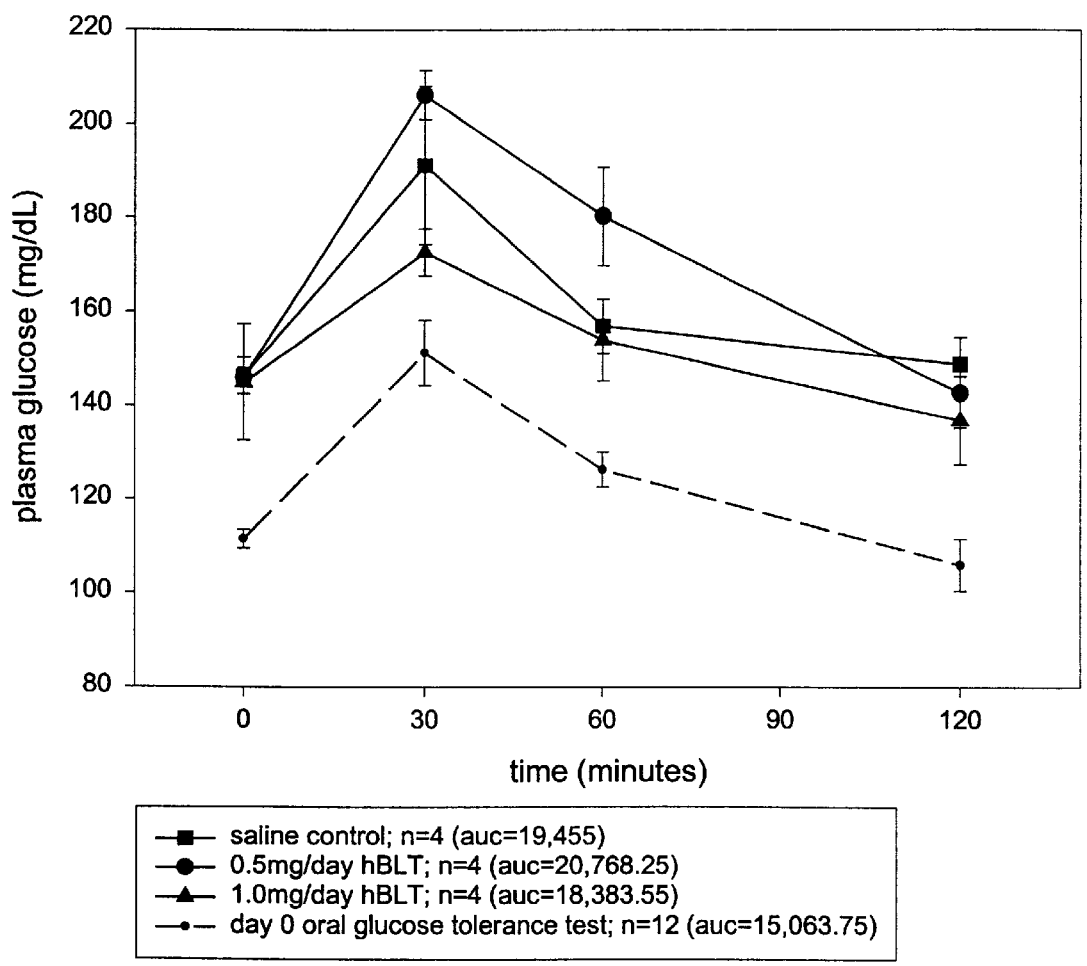
FIG. 16. Plasma glucose values in oral glucose tolerance test after Alzet pump continuous administration of human betalipotropin for 5 days in male ZDF rats.

Recombinant Vector pHMM260-ProCpB(10)/LVPR/ Beta lipotropin (R49) Encoding Procarboxypeptidase-BLT Fusion Protein A recombinant DNA expression vector, pHMM260, contains a ProCpB(10)/LVPR/Beta Lipotropin (R49) expression cassette, encoding a procarboxypeptidase-BLT fusion protein. This vector was produced using standard cloning techniques. An annotation of the expression cassette of pHMM260 is shown in FIG. 16. The expression cassette is flanked by an NdeI site at the 5' end and a BamHI site at the 3' end. The pro-peptide portion of porcine Procarboxypeptidase B protein occurs at the 5' end of the cassette, beginning with a Met residue and ending with a Ser residue. A thrombin protease recognition sequence, LVPR, occurs immediately 3' of the procarboxypeptidase sequence. The sequence beginning with a Glu residue to the 3' end of the thrombin cleavage site encodes wild-type human beta-lipotropin.

Several derivative cassettes were constructed such that position 49 of the BLT sequence was changed from the wild type sequence Arg (R49) to Ala (A49) pHMM261, or Glu (E49) pHMM262, or Gln (Q49) pHMM263. These derivative were made in order to reduce susceptibility to proteolysis during synthesis and purification of the fusion proteins. All of these vectors encode soluble fusion proteins.

EXAMPLE 5

Recombinant Vector pHMM268 Encoding Serine Hydroxy Methyltransferase(SHMT)-BLT Fusion Protein A fusion protein containing an amino-terminal sequence from the enzyme serine hydroxy methylase transferase (SHMT) was constructed using standard cloning techniques. The plasmid pHMM268 was expressed at high levels in *E. coli*. The fusion protein produced by pHMM268 was insoluble and could be recovered with the particulate fraction. This feature provided advantage in protection against proteolytic degradation.

EXAMPLE 6

Administration of Mouse BLT for 7 Days to Male $A^{vy/A}$ Mice

The $A^{vy/A}$ mouse is a model for obesity and diabetes. This inbred strain develops hyperglycemia, hyperinsulinemia, and insulin insensitivity in mid-life, and therefore provides a useful model for both obesity and diabetes.

Male $A^{vy/A}$ mice were purchased from Harlan Co. (Indianapolis, Ind.) at about 6 months of age. The animals were housed, 6 per cage, and fed ad libitum 5008 feed and water. Blood glucose levels were measured at regular intervals; when morning glucose levels reached at least 300 mg/dL the animals were subjected to the experimental protocol. Five animals, randomly selected, were housed together as a control; 5 animals, randomly selected, were housed together to receive treatment with mouse BLT (the mouse BLT sequence is readily available; See e.g. M. Notake et. al. FEBS Lett. 156, 67–71, 1983; herein incorporated by reference), synthesized by solid phase techniques.

Mice undergoing treatment with BLT received 60 μg bid subcutaneously (SC) (200 μl total volume for each dose); control animals received 200 μl vehicle bid(saline solution). The animals were injected twice daily, in the morning and in the afternoon, for 6 days; on day 7 they received just the morning injection.

Blood glucose levels, body weight, and food consumption were measured in the morning on day 0. Body weight and food consumption were measured in the morning on days 1 through 6. Plasma triglycerides were measured in the morning of day 6. Mice were fasted overnight from the afternoon of day 6 to the morning of day 7. On day 7, an oral glucose tolerance test was performed. Zero time blood glucose levels were measured 2 hours after the morning injection of either saline or BLT. For this test, animals were administered oral 25% dextrose solution (100 μl/10 g body weight), then bled 30, 60, and 120 minutes later. The blood samples were used for determining levels of glucose and insulin. After the oral glucose tolerance test, the animals were fed ad libitum. On days 1, 3, and 14 after the last SC injection, of either saline or BLT, animals were bled to determine blood glucose values.

Results

BLT Administration Lowers Blood Glucose and Insulin In Vivo

The results of these experiments are summarized in FIGS. 1–8. Throughout the course of the 7 day treatment, animals in the control group and the test group consumed roughly 4.5 to 6 grams of food (FIG. 1). Body weight in both groups remained the same in both groups, at about 50 grams (FIG. 2).

BLT treatment decreased plasma triglycerides in treated mice after 6 days of treatment (see FIG. 3). The control animals exhibited a mean value of 3.05 nmol/L (s.d. 0.58), whereas treated animals were measured at a mean value of 2.05 nmol/L (s.d. 0.43). This represents a decline in serum triglycerides of about 30% to 35%.

Figure 4:
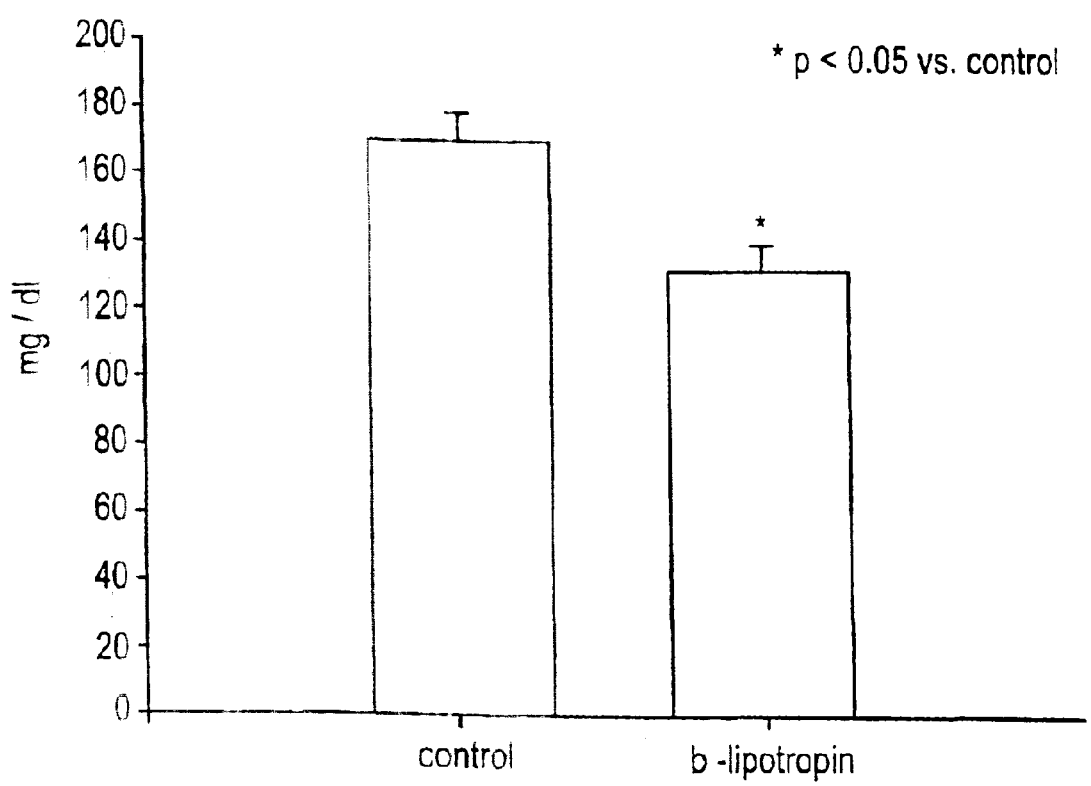
FIG. 4. Mouse betalipotropin decreases blood glucose in male Avy/a mice after seven days of administration.

BLT also induced a substantial decline in blood glucose levels in treated animals (FIG. 4). After 7 days of administration of BLT the treated group manifested blood glucose levels of 135 mg/dL (s.d. 16); in marked contrast the control group measured at 171 mg/dL (s.d. 16).

Figure 5:
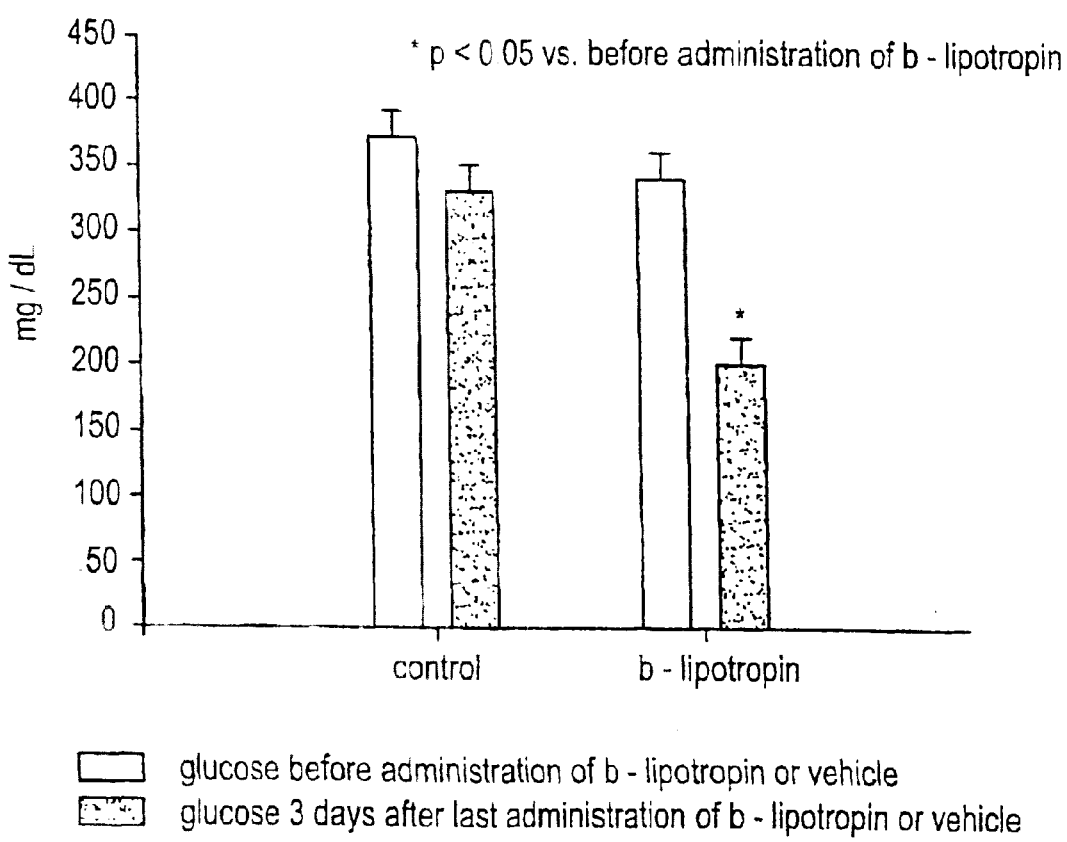
FIG. 5. Blood glucose values after 3 days in male Avy/a mice before and after 7 days administration of mouse betalipotropin.
Figure 6:
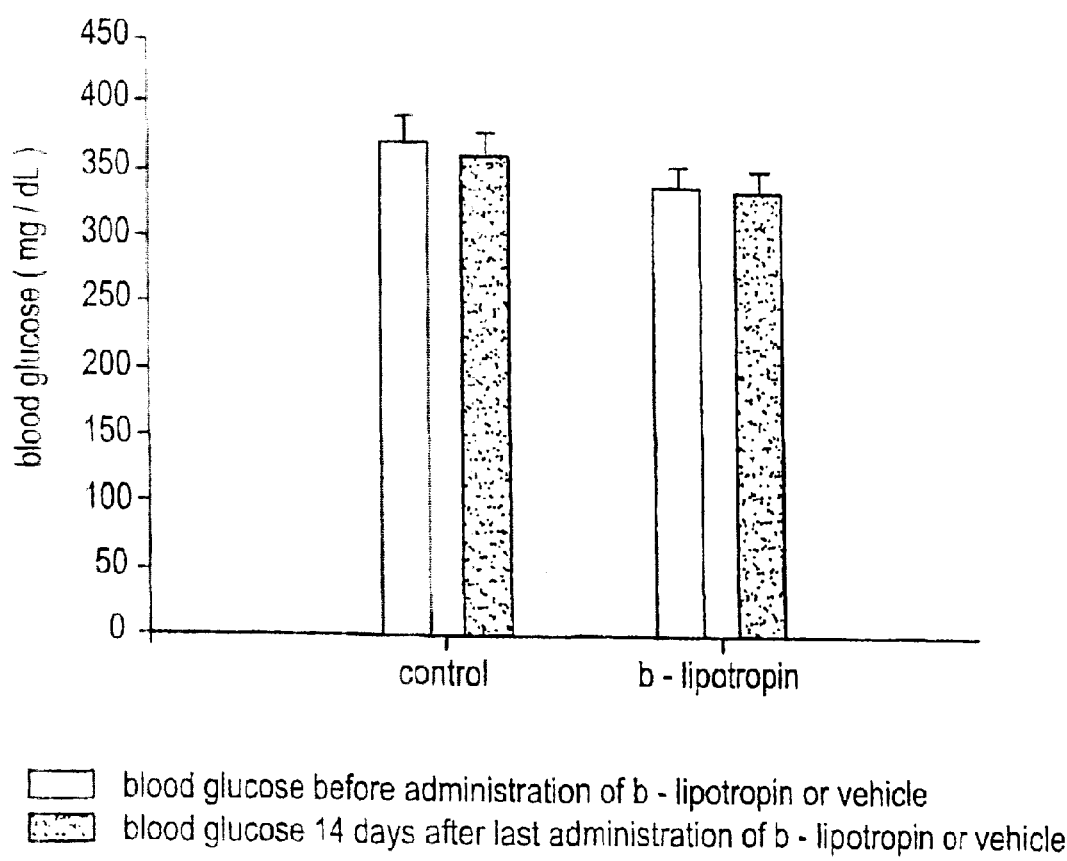
FIG. 6. Blood glucose values after 14 days in male Avy/a mice before and after 7 days administration of mouse betalipotropin.

The decline in blood glucose levels in treated animals continued for at least 3 days after the last administration of BLT on day 7 (FIG. 5). The control animals exhibited glucose levels of 331 mg/dL (s.d. 79). On the other hand, treated animals maintained substantially lower blood glucose levels, at 205 mg/dL (s.d. 76). The effect of BLT in lowering blood glucose levels was not observed at 14 days after the last administration of BLT (FIG. 6).

Figure 7:
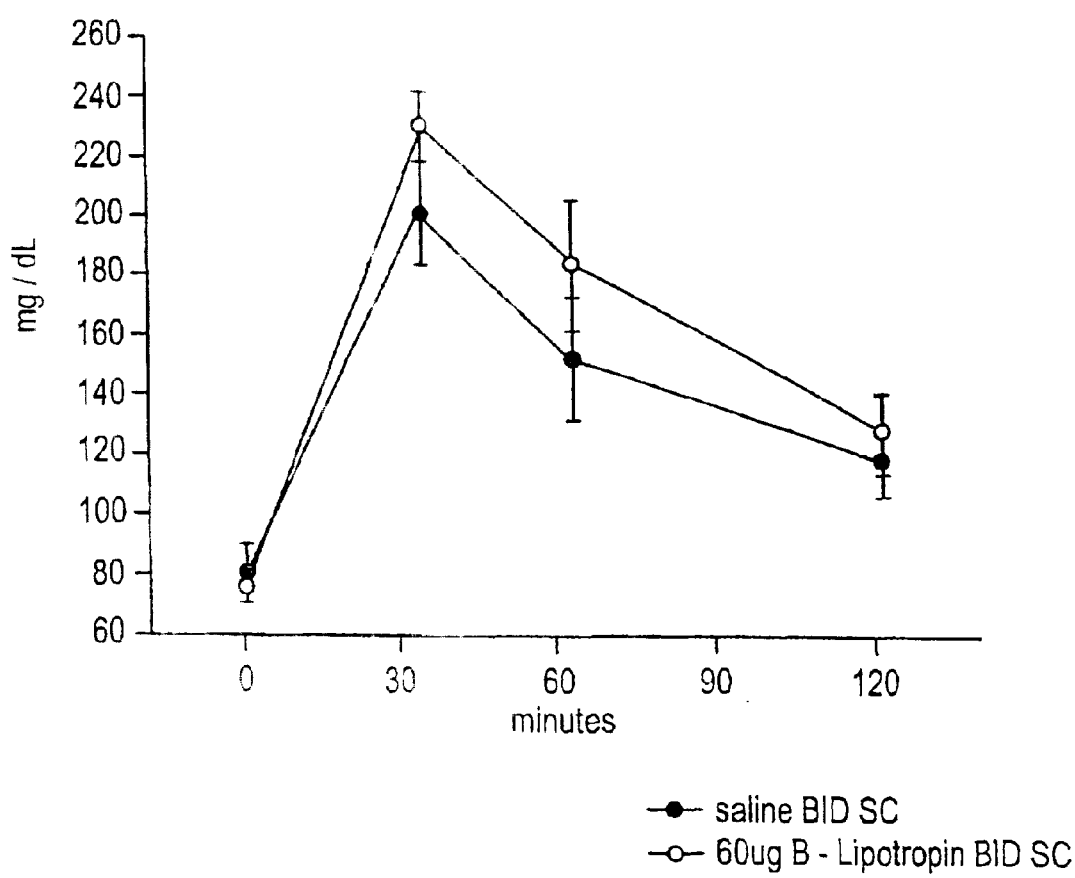
FIG. 7. Blood glucose values in oral glucose tolerance test after 7 days administration of betalipotropin and overnight fast.
Figure 8:
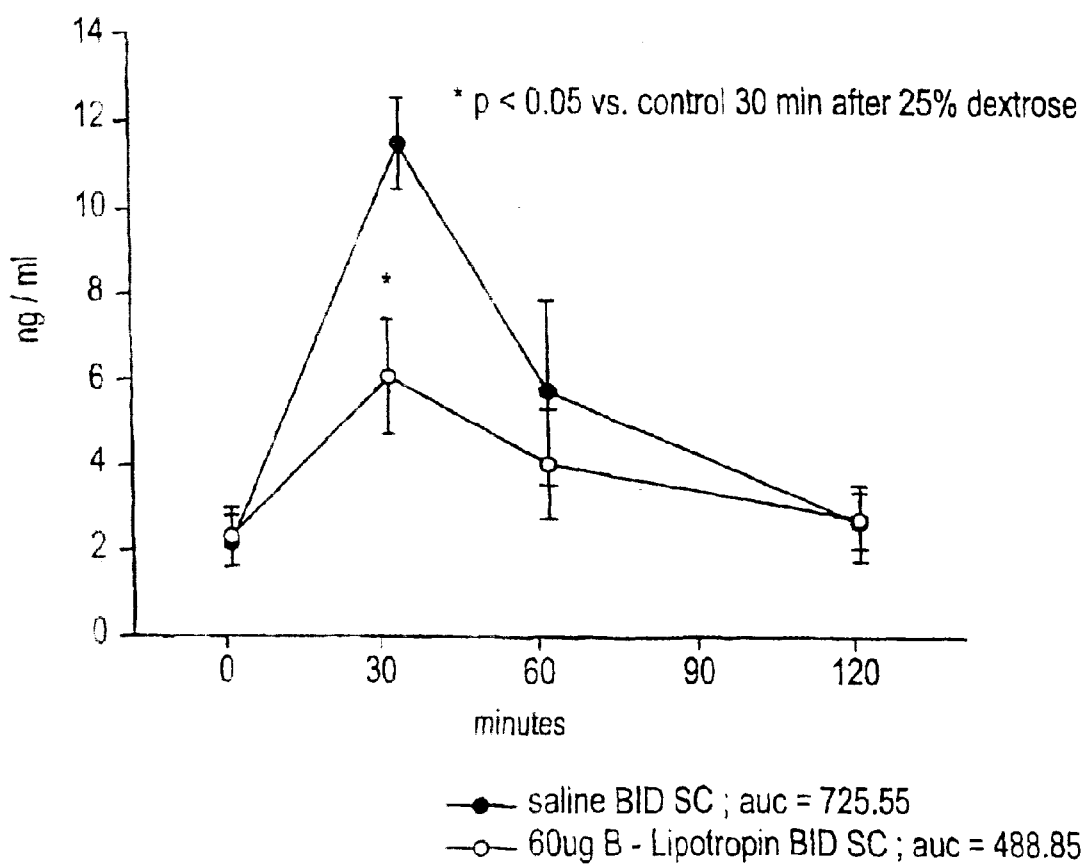
FIG. 8. Plasma insulin values in oral glucose tolerance test after 7 days administration of betalipotropin and overnight fast.

To address the effects of BLT treatment on insulin levels, an oral glucose tolerance test was performed after the 7 day treatment period and an overnight fast (FIG. 7 and FIG. 8). Control and treated animals showed an initial rise in blood glucose levels from about 80 mg/dL to 200 mg/dL, or greater, at the 30 minute time point after initiation of the test; thereafter both groups showed a comparable rate of decline in values, out to the 2 hour time point (FIG. 7). Strikingly, the treated animals exhibited plasma insulin values substantially below the control animals (FIG. 8). For example, at the 30 minute time point, control animals had insulin levels at 11.5 ng/ml (s.d. 1.9), whereas treated animals had insulin levels of 6.0 ng/ml (s.d. 3.0).

EXAMPLE 7

Administration of Mouse BLT for 14 Days to Male $A^{vy/A}$ Mice

Male $A^{vy/A}$ mice were housed, 6 per cage, and fed ad libitum 5008 feed and water. Blood glucose levels were measured at regular intervals; when morning glucose levels reached at least 300 mg/dL the animals were subjected to the experimental protocol. Five animals, randomly selected, were housed together as a control; 5 animals, randomly selected, were housed together and treated with mouse BLT, which had been synthesized by solid phase techniques.

Mice undergoing treatment with BLT received 60 μg bid SC (200 μl total volume for each dose); control animals received 200 μl vehicle (saline solution). The animals were injected twice daily, in the morning and in the afternoon, for 13 days; on day 14 they received just the morning injection.

Blood glucose levels, body weight, and food consumption were measured in the morning on day 0. Body weight and food consumption were measured in the morning on days 1 through 13. Mice were fasted overnight from the afternoon of day 13 to the morning of day 14. On day 14, an oral glucose tolerance test was performed. Zero time blood glucose levels were measured 2 hours after the morning injection of either saline or BLT. For this test, animals were administered oral 25% dextrose solution (100 μl/10 log body weight), then bled 30, 60, and 120 minutes later. Blood samples were used for determining levels of glucose and insulin. After the oral glucose tolerance test, the animals were fed ad libitum. On days 1, 3, and 14 after the last SC injection, of either saline or BLT, animals were bled to determine blood glucose values.

Results

BLT Administration for 14 Days Lowers Blood Glucose and Insulin

Figure 9:
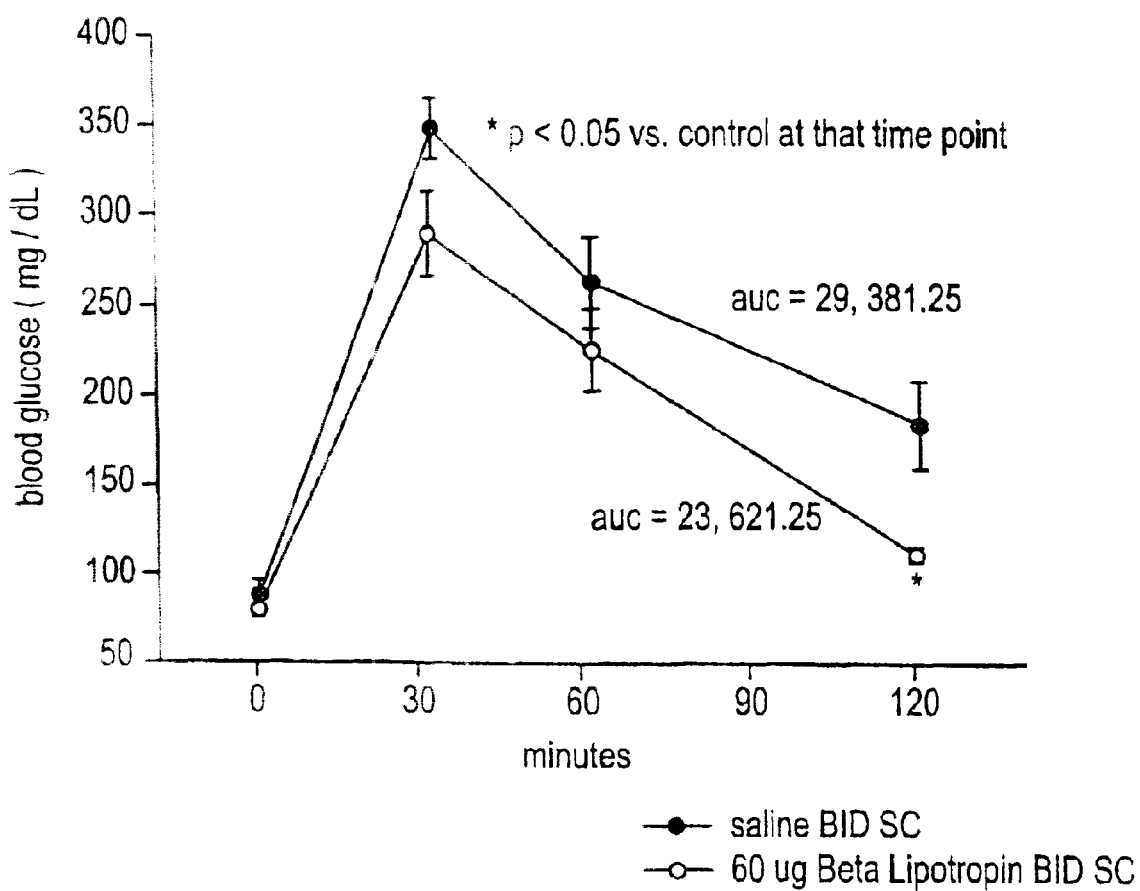
FIG. 9. Blood glucose values in oral glucose tolerance test after 14 days administration of betalipotropin and overnight fast.
Figure 10:
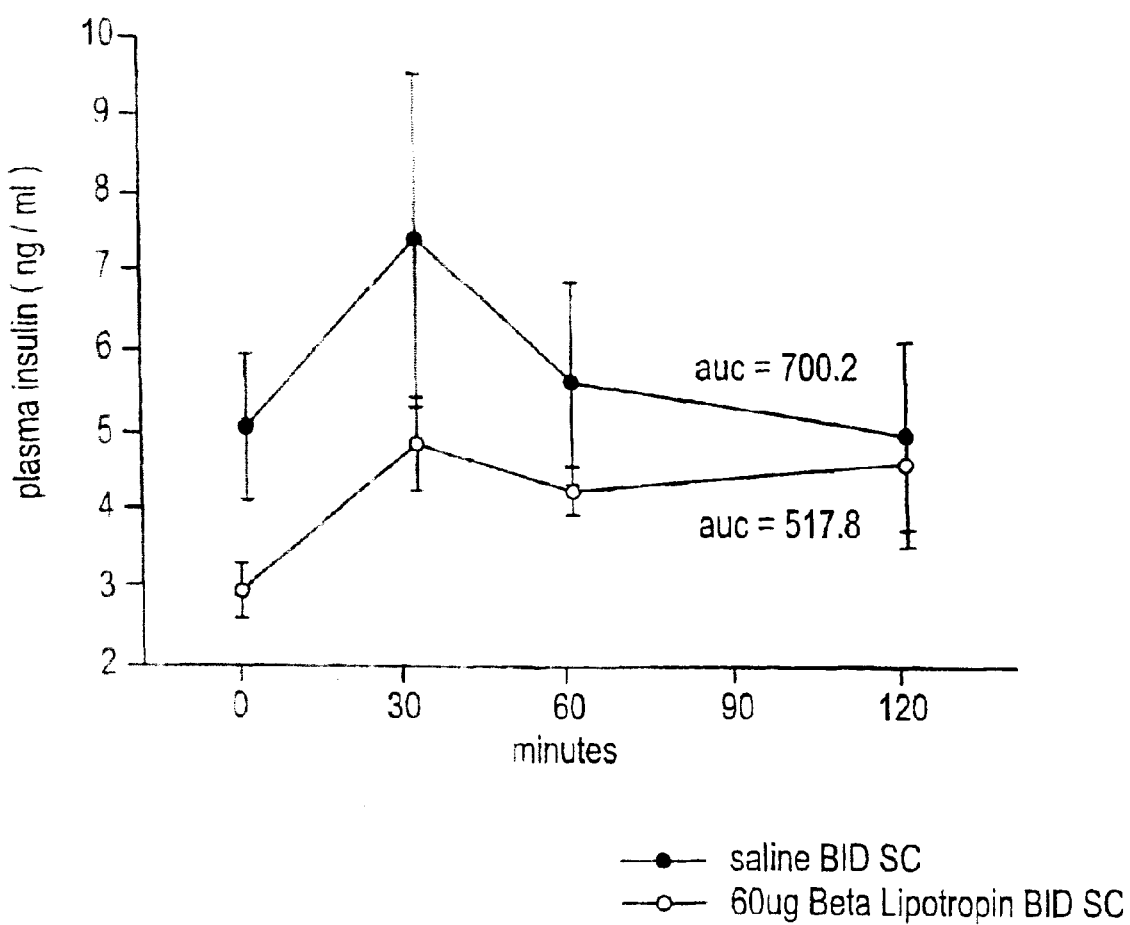
FIG. 10. Plasma insulin values in oral glucose tolerance test after 14 days administration of betalipotropin and overnight fast.

The results are summarized in FIGS. 9–10. Throughout the 14 day treatment, animals in the control group and the test group consumed roughly 4.5 to 6 grams of food and body weights in both groups remained the same in both groups, at about 50 grams (data not shown).

To address the effects of a two week treatment with BLT on insulin levels, an oral glucose tolerance test was performed after the 14 day period (FIG. 9 and FIG. 10). Control and treated animals showed an initial rise in blood glucose levels from about 80 mg/dL to 300 mg/dL, or greater, at the 30 minute time point; thereafter both groups showed a comparable rate of decline in values, out to the endpoint of the test at 2 hours (FIG. 9). For example, treated animals showed an average blood glucose level at the 30 min. time point of 289 mg/dL (s.d. 24), whereas controls had levels of 348 mg/dL (s.d. 18). Lower levels were observed at the 60 min. and 120 min. time points also. For example, at 120 min. treated animals had average blood glucose levels of 114 mg/dL (s.d. 4), whereas controls had levels of 188 mg/dL (s.d. 23).

Treated animals also exhibited plasma insulin values substantially below the control animals (FIG. 10). For example, at the 30 minute time point, control animals had insulin levels at 7.4 ng/ml (s.d. 2.1), whereas treated animals had insulin levels of 4.8 ng/ml (s.d. 0.6).

EXAMPLE 8

BLT Stimulates Glucose Uptake in 3T3 Adipocytes

Mouse 3T3-L1 cells were plated in about 100 μl of growth medium per well in 96 well plates such that about 25,000 cells were distributed per well.

Growth Medium:
 DMEM, high glucose, w/out L-glutamine
 10% Calf serum
 2 mM L-glutamine
 1% PenStrep
 1.25 μg/ml Fungizone Cells were induced to differentiate into adipocytes 3 days after plating by replacing growth medium with Differentiation medium.

Differentiation Medium:
 DMEM, high glucose, w/out L-glutamine
 10% FBS 2 mM L-glutamine
1% Pen Strep
1.25 μg/ml Fungizone
10 mM Hepes
0.25 μM dexamethasone (1 μl/ml of 0.25 mM stock)
0.5 mM IBMX (10 μl/ml of 50 mM stock)
5 μg/ml insulin (1 μl/ml 5 mg/ml stock)

Medium was removed from cells by aspiration using an 8 channel manifold attached to a house vacuum source with a flow regulator. Fresh medium was dispensed into wells using an 8 channel Matrix electronic pipettor, set to the slowest speed, so as to minimize disruption of cells.

On day 1, 100 μl Differentiation medium was added to each well to initiate differentiation of 3T3 cells into adipocytes. On day 3 after the start of differentiation, the medium was changed to Differentiation medium containing insulin, but without IBMX or dexamethasone (Insulin media). On day 6, the medium was again changed to Differentiation medium containing no insulin, IBMX, or dexamethasone (FBS medium). Cells were maintained in FBS medium, with feeding every other day, until ready for a glucose transport assay from days 15 to 21 after the start of differentiation.

EXAMPLE 9

Glucose Transport Assay in 3T3 Cells Induced to Differentiate into Adipocytes in the Presence of BLT Mouse 3T3-L1 cells were induced to differentiate into adipocytes as in Example 8. At 15–24 hours prior to conducting a glucose transport assay, cells were treated as follows:

1. Wells were washed twice with 100 ml phosphate buffered saline (PBS) at 37° C., aspirating between washes.
2. Next, 100 ml DMEM, high glucose, 1% Antibiotic/Antimycotic solution, 2 mM glutamine, 0.1% BSA (warmed to 37° C.), 0 to 1000 nM mouse BLT (synthesized by solid phase technique), and 0 to 100 nM insulin was added to each well. This is the serum starvation phase.
3. Then, cells were incubated overnight at 37° C.

On the day of assay, cells were treated as follows:

1. Medium was removed, plates were blotted on paper towels, and cells were washed twice with 100 ml KRBH buffer (Krebs-Ringer buffer containing Hepes, pH 7.4).
2. After removing the final wash, the cells were incubated at 37° C. for 1 hour in 100 μl KRBH, 0.1% BSA with 100 μM glucose, 10 μl/ml (0.1 μCi/well) radiolabeled 2-Deoxyglucose ($C^{14}$), and desired insulin concentrations.
3. Following incubation with radiolabeled glucose, 10 μl of 10× cytochlasin B (200 μM) was added to stop further glucose uptake by cells.
4. Radiolabeled glucose uptake was determined by reading plates on a Microbeta plate reader.

Results

Figure 11:
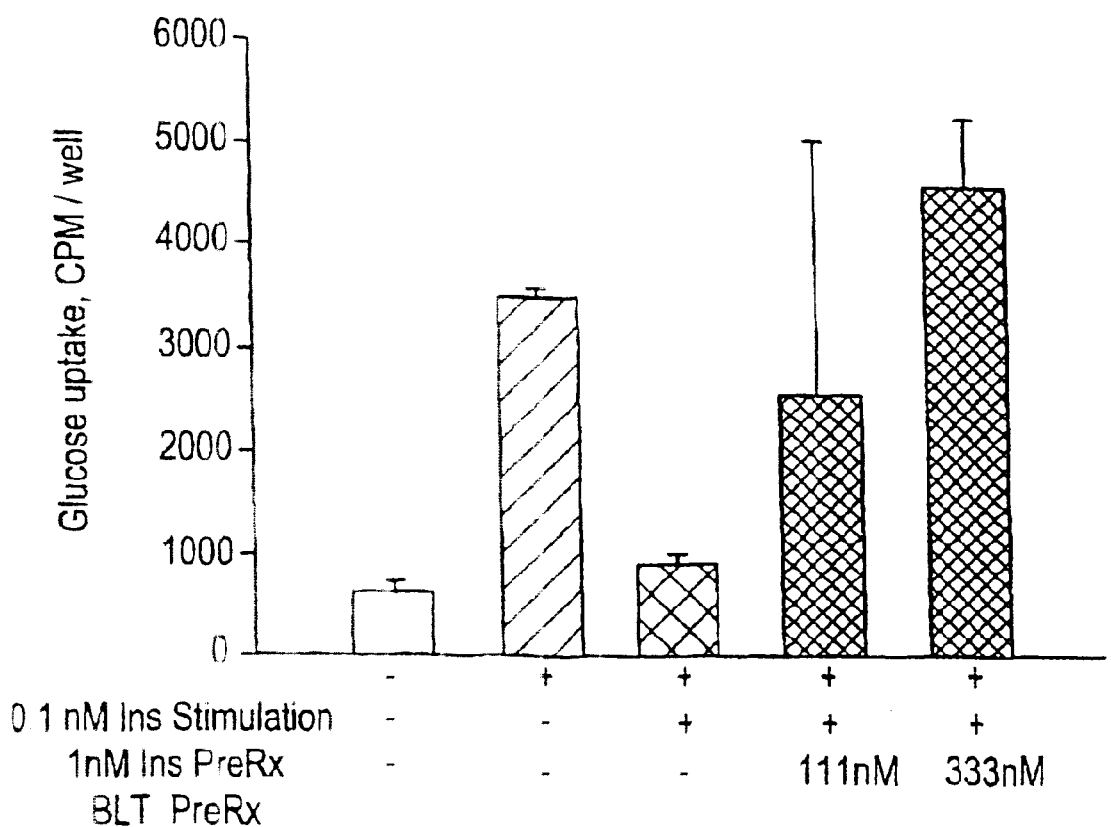
FIG. 11. Betalipotropin pretreatment enhances glucose uptake in 3T3-L1 adipocytes that have been pretreated with insulin.

The results of this experiment are summarized in FIG. 11. Glucose uptake into 3T3 cells induced to differentiate into adipocytes was stimulated from about 3-fold to about 6-fold when the adipocytes were pretreated prior to the uptake assay with BLT.

EXAMPLE 10

Glucose Transport Assay in 3T3 Cells Induced to Differentiate into Adipocytes in the Presence of Functional Fragments of BLT Mouse 3T3-L1 cells are induced to differentiate into adipocytes as in Example 8. About 15–24 hours prior to conducting a glucose transport assay, cells are treated as follows:

1. Wells are washed twice with 100 ml phosphate buffered saline (PBS) at 37° C., aspirating between washes.
2. Next, 100 ml DMEM, high glucose, 1% Antibiotic/Antimycotic solution, 2 mM glutamine, 0.1% BSA (warmed to 37° C.), 0 to 1000 nM mouse or human BLT (synthesized by solid phase technique), and 0 to 100 nM insulin is added to each well. This is the serum starvation phase. For example, in one test human BLT fragment designated herein as SEQ ID NO:10 is used; in another test, human BLT fragment designated herein as SEQ ID NO:12 is used.
3. Then, cells are incubated overnight at 37° C.

On the day of assay, cells are treated as follows:

1. Medium is removed, plates are blotted on paper towels, and cells are washed twice with 100 ml KRBH buffer (Krebs-Ringer buffer containing Hepes, pH 7.4).
2. After removing the final wash, the cells are incubated at 37° C. for 1 hour in 100 μl KRBH, 0.1% BSA with 100 μM glucose, 10 μl/ml (0.1 μCi/well) radiolabeled 2-Deoxyglucose ($C^{14}$), and desired insulin concentrations.
3. Following incubation with radiolabeled glucose, 10 μl of 10× cytochlasin B (200 μM) is added to stop further glucose uptake by cells.
4. Radiolabeled glucose uptake is determined by reading plates on a Microbeta plate reader.

Results

Glucose uptake into 3T3 cells induced to differentiate into adipocytes is enhanced over the controls when adipocytes are pretreated prior to the uptake assay with functional fragments of BLT.

EXAMPLE 11

Functional Analogs of BLT

Mouse 3T3-L1 cells are induced to differentiate into adipocytes as in Example 10. Adipocytes are then exposed to analogs of human BLT, for example, SEQ ID NO:26 through SEQ ID NO:35 and glucose transport is monitored as in Example 8. Functional analogs exhibit substantially the same results as native BLT.

EXAMPLE 12

Administration of Human BLT for 14 Days to Male A/A Mice

Solid-phase synthesized human BLT was administered to male $A^{vy/A}$ mice in the dosage and according to the regimen described in Example 7.

Results

Figure 12:
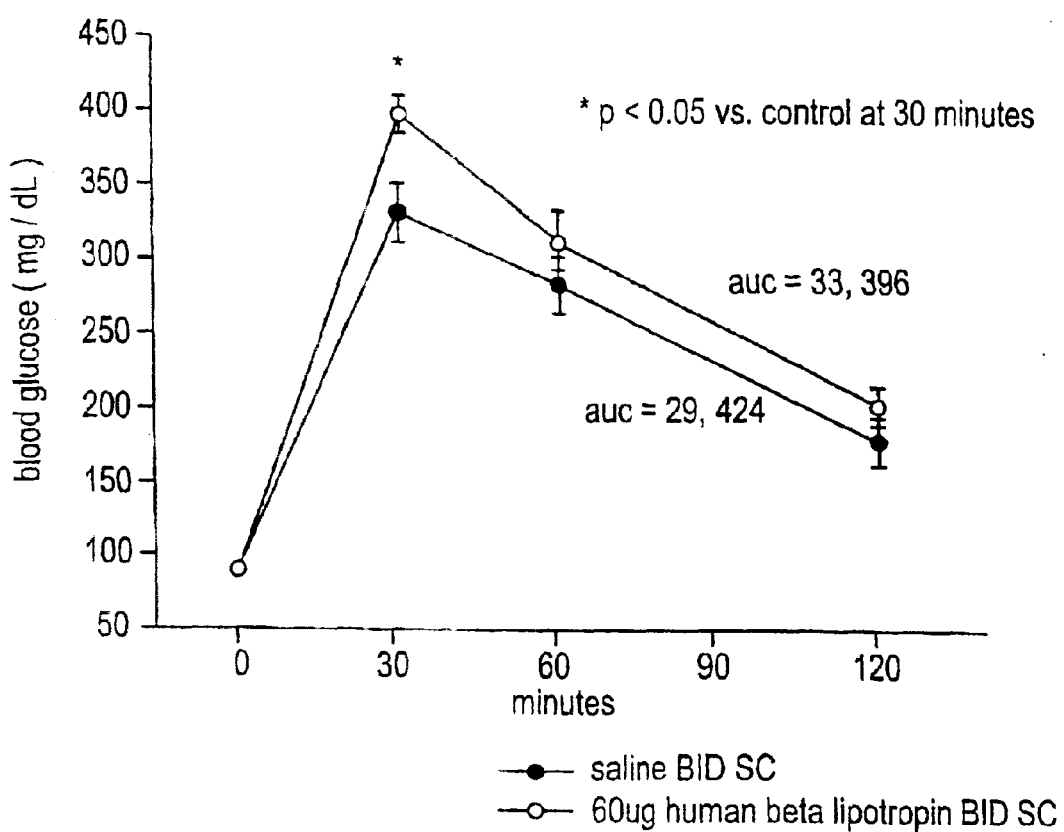
FIG. 12. Blood glucose values in oral glucose tolerance test after 14 days administration of human betalipotropin and overnight fast.
Figure 13:
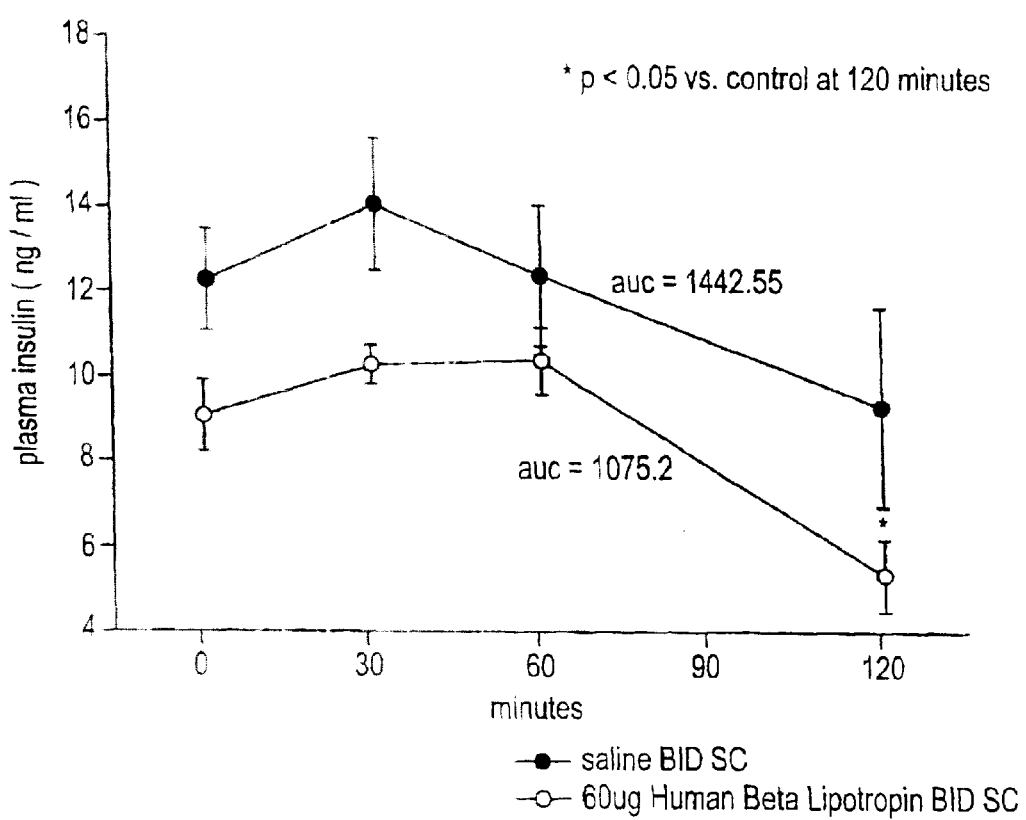
FIG. 13. Plasma insulin values in oral glucose tolerance test after 14 days administration of human betalipotropin and overnight fast.

Human BLT administration lowered substantially serum insulin levels in male $A^{vy/A}$ mice (See FIGS. 12 and 13).

The results are summarized in FIGS. 12–13. Throughout the 14 day treatment, animals in the control group and the test group consumed roughly 4.5 to 6 grams of food and body weights in both groups remained the same in both groups, at about 50 grams (data not shown).

To address the effects of a two week treatment with human BLT on plasma glucose and insulin levels, an oral glucose tolerance test was performed after the 14 day period. Control animals and treated animals showed an initial rise in blood glucose levels from about 80 mg/dL to 300 mg/dL, or greater, at the 30 minute time point; thereafter both groups showed a comparable rate of decline in values, out to the endpoint of the test at 2 hours (FIG. 12). For example, treated animals showed an average blood glucose level at the 30 min. time point of about 400 mg/dL (s.d. 12), whereas controls had levels of 330 mg/dL (s.d. 19). Lower levels were observed at the 60 min. and 120 min. time points also. For example, at 120 min. treated animals had average blood glucose levels of 178 mg/dL (s.d. 16), whereas controls had levels of 202 mg/dL (s.d. 13).

Treated animals exhibited plasma insulin values substantially below the control animals (FIG. 13). For example, at the 30 minute time point, control animals had insulin levels at 14.0 ng/ml (s.d. 1.5), whereas treated animals had insulin levels of 10.2 ng/ml (s.d. 0.4). At the 120 minute time point, control animals had insulin levels at 9.3 ng/ml (s.d. 2.3) and treated animals had insulin levels of 5.4 ng/ml (s.d. 0.9).

EXAMPLE 13

Mouse Beta Lipotropin Administration to Male $Lep^{ob}/Lep^{ob}$ Mice

Male $Lep^{ob}/Lep^{ob}$ mice purchased from Jackson Laboratories (Bar Harbor, Me.) were housed singly and fed ad libitum 5008 feed and water. Mice were tail bled for initial glucose, insulin, and triglyceride values. Mice were selected for either control, 60 $\mu$g, or 120 $\mu$g bid mouse beta lipotropin treatment. Treated mice received either 60 $\mu$g bid SC or 120 $\mu$g bid SC (200 $\mu$l total volume each dose); control mice received 200 $\mu$l vehicle (saline). Mice were injected at 7:00 am and 3:00 pm daily for 16 days, and injected at 7:00 am only on day 17. Body weight and food consumption were measured in the morning on days 0 through 17. Mice were tail bled the morning of day 7 for blood glucose, insulin, and triglyceride values. The animals were fasted overnight from the afternoon of day 13 to the morning of day 14. On day 14, an oral glucose tolerance test was performed. Zero time blood glucose and insulin were measured 2 hours after the morning injection. Mice were administered oral 25% dextrose solution (100 $\mu$l/10 g body weight), then bled 30, 60, and 120 minutes later. Blood samples were used for determining glucose and insulin. After the oral glucose tolerance test, the mice were fed ad libitum. On day 16, tail blood samples were taken to determine blood glucose, insulin, triglyceride, and corticosterone values. On day 17, the mice were sacrificed.

Figure 14:
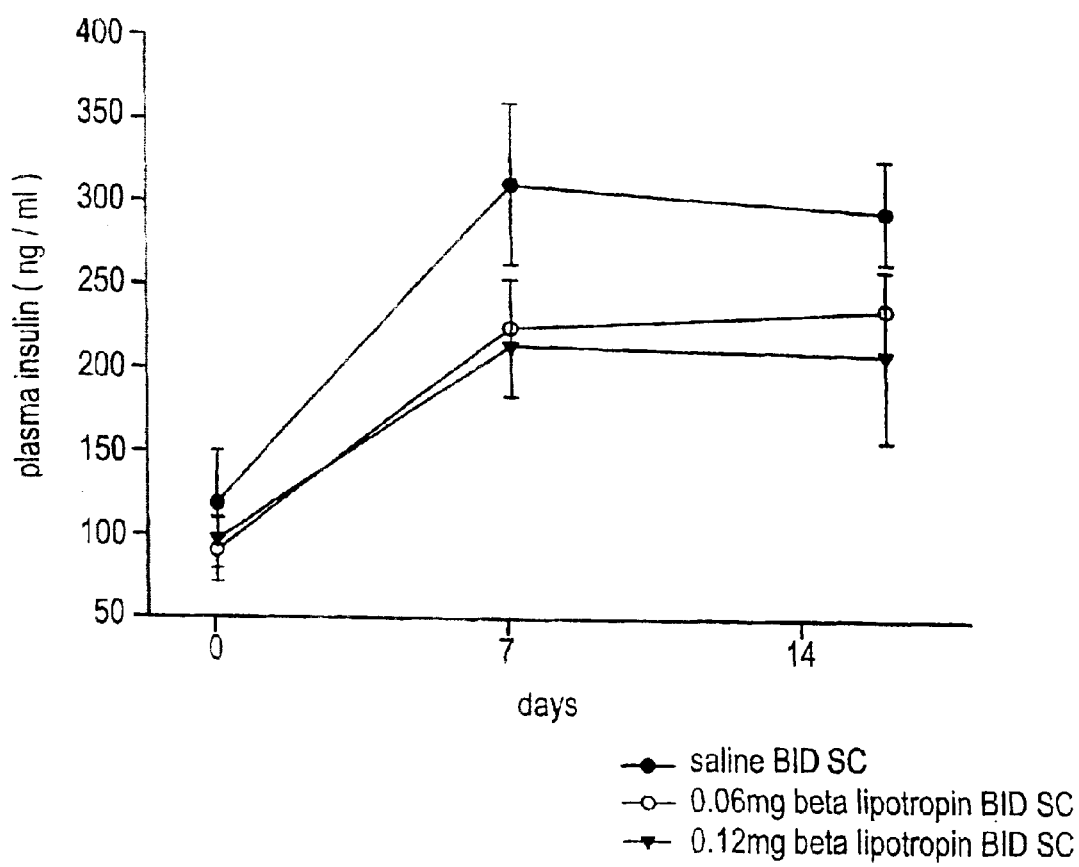
FIG. 14. Plasma insulin values in male $Lep^{ob}/Lep^{ob}$ mice after 16 days administration of mouse betalipotropin.

The results from this experiment are shown in FIG. 14. Plasma insulin values were significantly lowered in the treated animals throughout the 16 day treatment period. For example, at day 7 of the treatment the control animals exhibited insulin values of about 300 ng/ml while treated animals were measured at about 215 ng/ml, at least a 30% diminution. Moreover, plasma insulin values remained lower in treated animals at day 16 of the treatment (FIG. 14).

EXAMPLE 14

Alzet™ Pump Administration of Human BLT to Male $Lep^{ob}/Lep^{ob}$ Mice

Male $Lep^{ob}/Lep^{ob}$ mice purchased from Jackson Laboratories(Bar Harbor, Ma.) at one month of age were housed singly and fed ad libitum 5008 feed and water with lighting on a 12 hour cycle (off from 6:00 pm to 6:00 am). Mice were tail bled for initial glucose, insulin, and triglyceride values. Treated animals received 0.24 mg/day or 0.48 mg/day continuous administration of human beta lipotropin (ER4-VBH-43) via subcutaneously implanted Alzet™ pumps (Alza, Inc.) so that the average glucose and triglyceride values were equal throughout all 3 groups. Control animals were given saline solution. The pumps were filled with saline for the control group, and 20 mg/ml human beta lipotropin for the low dose group, and 40 mg/ml human beta lipotropin for the high dose group. Mice were anesthetized with isoflurane prior to implantation of the pump. Body weight and food consumption were measured on the morning of days 0 through 7. Mice were tail bled the morning of day 4 for blood glucose, insulin, and triglyceride values. Mice were fasted overnight from the afternoon of day 6 to the morning of day 7.

On day 7, an oral glucose tolerance test was performed. Mice were tail bled for 0 time insulin and glucose, then administered oral 25% dextrose solution (100 $\mu$l/10 g body weight), then bled 30, 60, and 120 minutes later. The blood samples were used for determining glucose and insulin. After the oral glucose tolerance test, the mice were fed ad libitum.

Figure 15A:
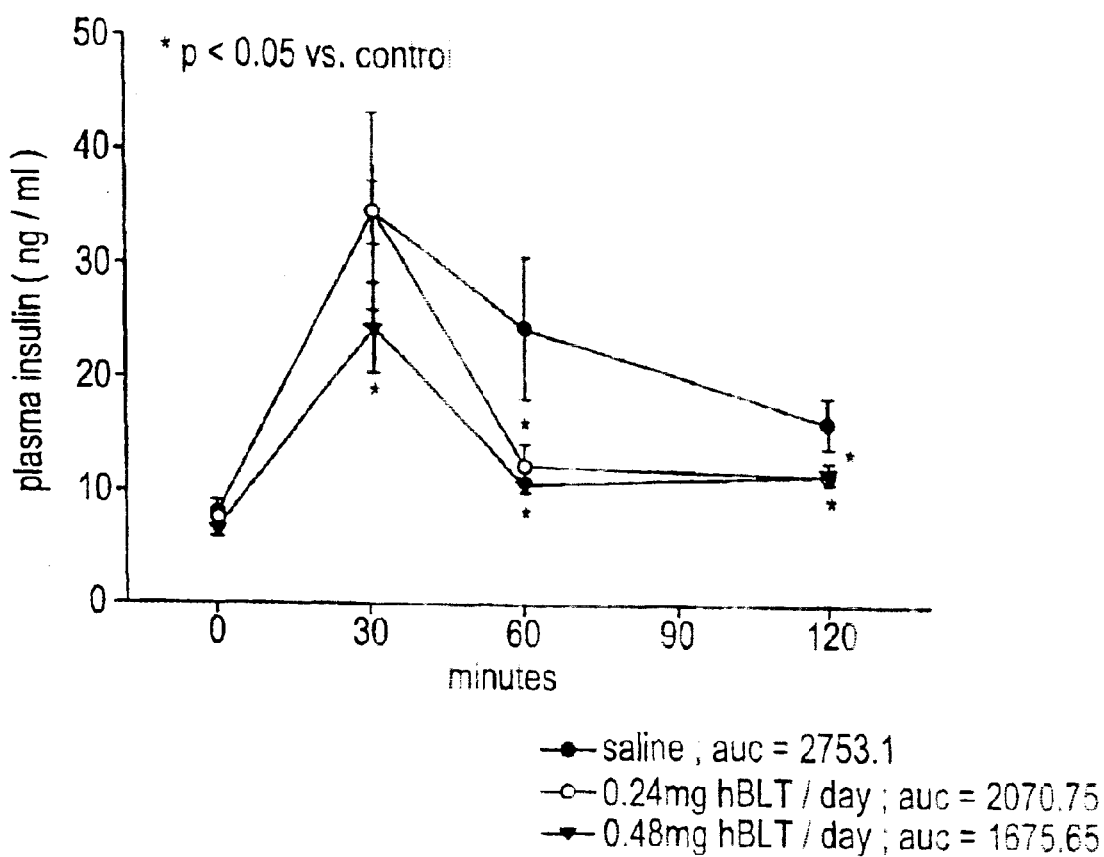
FIG. 15. Glucose and insulin values in oral glucose tolerance test after Alzet pump continuous administration of human betalipotropin for 6 days.
Figure 15B:
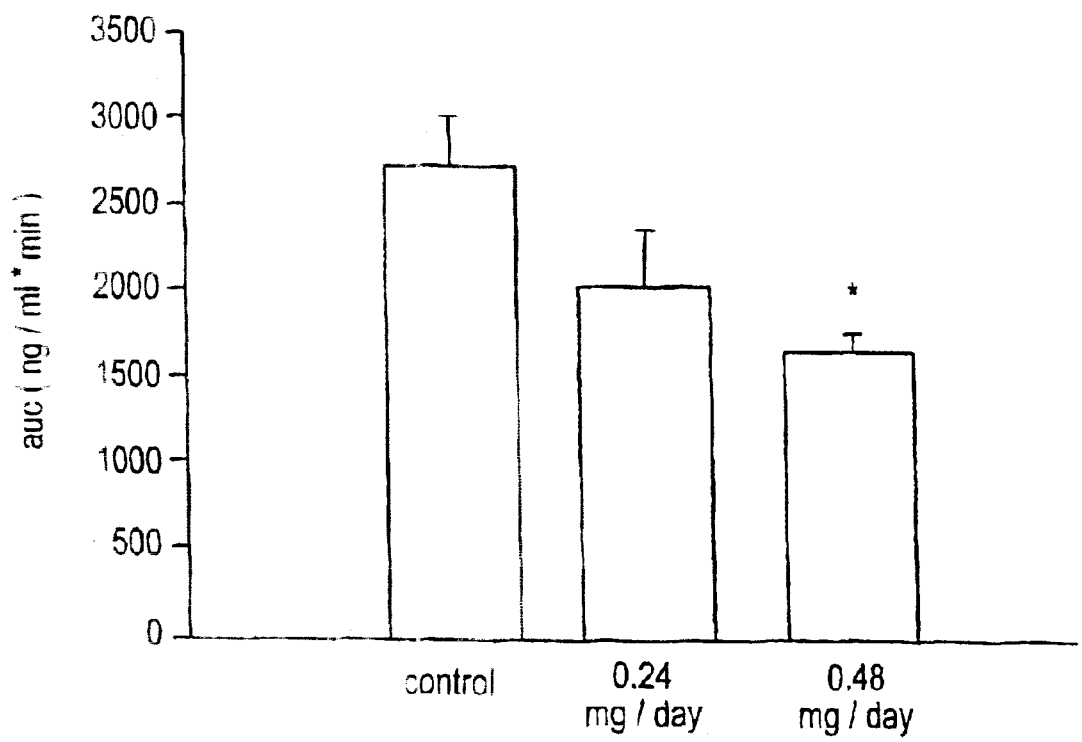

The results of the glucose tolerance test respecting plasma insulin levels are shown in FIG. 15. The value at 0.24 mg BLT/day was about 25% lower than the control, while the value at 0.48 mg BLT/day was about 40% lower than the control (see FIG. 15 inset for area under curves).

EXAMPLE 15

Solid Phase Synthesis and Purification of an analog of Human BLT Protein

An analog of human BLT peptide (i.e. the analog represented by SEQ ID NO:26), in which Ala is substituted for Glu in SEQ ID NO:8, was synthesized in a single run using Fmoc chemistry. The synthesis is complicated by the presence of several asp-gly dipeptide sequences in the N-terminal portion of the peptide. Aspartyl side chains in asp-gly didpeptide sequences have been observed to undergo base catalyzed cyclization and subsequent addition with piperidine during FMOC synthesis. This reaction is eliminated by use of Fmoc-(FmocHmb)-glycine at each asp-gly sequence in the synthesis. Protection of the glycyl amide with the Hmb group inhibits the cyclization of the aspartyl side chain. Following cleavage, deprotection, and reverse phase HPLC purification, the peptide can be analyzed by electrospray mass spectrometry. The major species seen in the synthesis is the full length peptide having the expected mass. Use of this method allows production of quantities of purified protein in excess of 100 mg from a single run at the 0.1 mmole scale.

Materials: Preloaded Fmoc-Glu (OtBu) Wang (1% cross-linked polystyrene functionalized with p-benzoxybenzyl alcohol) resin at approximately 0.6 mmole amino acid/g resin. N-methylpyrrolidone (NMP), piperidine, 2-(1H-benzotriazol-1-yl)-1,1,3,3-tetramethyluronium hexafluorophosphate (HBTU), 2M N,N-Diisopopylethylamine (DIEA) 1-hydroxybenzotriazole (HOBt), Dichloromethane (DCM), Dimethylformamide (DMF).

Resin, preloaded with the Fmoc-protected C-terminal amino acid (0.1 or 0.25 mmole amino acid), was weighed and placed into a reaction chamber. The resin was preswollen by washing with DCM. The resin was then washed with NMP. The N-terminal Fmoc group was removed by incubation of the resin in a 18–22 % solution of piperidine in NMP. Following deprotection, the resin was extensively washed with NMP.

One mmole of the next Fmoc-protected amino acid to be added to the peptide was solubilized in 2.1 g of NMP, 2.0 g of 0.45 M HBTU/HOBt reagent in DMF. Following the solubilization, activation of the amino acid was initiated by addition of 3 ml of 2M DIFA in NMP. The activated amino acid was then added to the deprotected resin and allowed to couple. Upon completion of coupling, the resin was washed extensively with NMP. The complete cycle of deprotection and coupling was then repeated for each successive amino acid.

Specific cycle steps in the synthesis were as follows:

| Cycle | AA | Steps |
|---|---|---|
| 1 | Ala | Complete wash |
| 2 | Gly | Single Couple |
| 3 | Lys(Boc) | Single Couple |
| 4 | Lys(Boc) | Single Couple |
| 5 | Tyr(tBu) | Single Couple |
| 6 | Ala | Single Couple |
| 7 | Asn(Trt) | Single Couple |
| 8 | Lys(Boc) | Single Couple |
| 9 | Ile | Single Couple |
| 10 | Ile | Single Couple |
| 11 | Ala | Single Couple |
| 12 | Asn(Trt) | Single Couple |
| 13 | Lys(Boc) | Single Couple |
| 14 | Phe | Single Couple |
| 15 | Leu | Single Couple |
| 16 | Thr(tBu) | Single Couple |
| 17 | Val | Single Couple |
| 18 | Leu | Single Couple |
| 19 | Pro | Double couple/Ac2O cap |
| 20 | Thr(tBu) | Single Couple |
| 21 | Gln(Trt) | Single Couple |
| 22 | Ser(tBu) | Single Couple |
| 23 | Lys(Boc) | Single Couple |
| 24 | Glu(OtBu) | Single Couple |
| 25 | Ser(tBu) | Single Couple |
| 26 | Thr(tBu) | Single Couple |
| 27 | Met | Single Couple |
| 28 | Phe | Single Couple |
| 29 | Gly | Single Couple |
| 30 | Gly | Single Couple |
| 31 | Tyr(tBu) | Single Couple |
| 32 | Arg(Pmc) | Single Couple |
| 33 | Lys(Boc) | Single Couple |
| 34 | Asp(OtBu) | Single Couple |
| 35 | Lys(Boc) | Single Couple |
| 36 | Pro | Double couple/Ac2O cap |
| 37 | Pro | Double couple/Ac2O cap |
| 38 | Ser(tBu) | Single Couple |
| 39 | Gly | Single Couple |
| 40 | Trp(Boc) | Single Couple |
| 41 | Arg(Pmc) | Single Couple |
| 42 | Phe | Single Couple |
| 43 | His(Trt) | Single Couple |
| 44 | Glu(OtBu) | Single Couple |
| 45 | Met | Single Couple |
| 46 | Arg(Pmc) | Single Couple |
| 47 | Tyr(tBu) | Single Couple |
| 48 | Pro | Double couple/Ac2O cap |
| 49 | Gly | Single Couple |
| 50 | Glu(OtBu) | Single Couple |
| 51 | Asp(OtBu) | Single Couple |
| 52 | Lys(Boc) | Single Couple |
| 53 | Lys(Boc) | Single Couple |
| 54 | Glu(OtBu) | Single Couple |
| 55 | Ala | Single Couple |
| 56 | Ala | Single Couple |
| 57 | Val | Single Couple |
| 58 | Leu | Single Couple |
| 59 | Leu | Single Couple |
| 60 | Ser(tBu) | Single Couple |
| 61 | His(Trt) | Single Couple |
| 62 | Glu(OtBu) | Single Couple |
| 63 | Leu | Single Couple |
| 64 | Asp(OtBu) | Single Couple |
| 65 | Ala | Single Couple |
| 66 | Gln(Trt) | Single Couple |
| 67 | Ala | Single Couple |
| 68 | Gly | Single Couple |
| 69 | Ala | Single Couple |
| 70 | Gly(Fmoc-hmb) | Double couple/Ac2O cap |
| 71 | Asp(OtBu) | Single Couple |
| 72 | Asp(OtBu) | Single Couple |
| 73 | Ala | Single Couple |
| 74 | Pro | Double couple/Ac2O cap |
| 75 | Gly(Fmoc-hmb) | Double couple/Ac2O cap |
| 76 | Asp(OtBu) | Single Couple |
| 77 | Pro | Double couple/Ac2O cap |
| 78 | Gly(Fmoc-hmb) | Double couple/Ac2O cap |
| 79 | Asp(OtBu) | Single Couple |
| 80 | Gly | Single Couple |
| 81 | Glu(OtBu) | Single Couple |
| 82 | Arg(Pmc) | Single Couple |
| 83 | Leu | Single Couple |
| 84 | Arg(Pmc) | Single Couple |
| 85 | Gln(Trt) | Single Couple |
| 86 | Gly | Single Couple |
| 87 | Thr(tBu) | Single Couple |
| 88 | Leu | Single Couple |
| 89 | Glu(OtBu) | Single Couple |
| 90 | | Final deprotect |

For amino acids that react slowly or inefficiently, 2 separate coupling reactions were performed. Any residual unreacted peptide was blocked by treatment with acetic anhydride. The sequence of steps for one of these amino acids was deprotection, coupling reaction 1, wash, coupling reaction 2, wash, Ac2O cap, wash, deprotection.

Abbreviations: OtBu: t-butyl ester, tBu: t-butyl, Boc: t-butoxycarbonyl, Pmc: 2,2,5,7,8-pentamethylchroma-6-sulfonyl, Hmb: 2-hydroxy-4-methoxybenzyl, Fmoc: 9-fluorenylmethoxycarbonyl.

EXAMPLE 16

Alzet Pump Administration of Human BLT to Male ZDF Rats

Male Zucker Diabetic Fatty (ZDF) rats, purchased from Genetic Models Inc. (Indianapolis, Ind.), were housed singly and fed ad libitum 5008 feed and water. At five weeks of age the rats were fasted overnight for an initial oral glucose tolerance test. Blood was withdrawn from the tail for determination of insulin and glucose levels at the 0 time point, and then the animals were administered oral 50% dextrose solution (2.5 g/kg body wt.), and blood withdrawn at 30, 60, and 120 minutes post-administration. After the oral glucose tolerance test, the rats were fed ad libitum. At 6 weeks of age, the animals were divided into groups of 4 animals each for administration of human BLT. On day zero of the test, tail blood was again withdrawn for the measurement of glucose, insulin, corticosterone, and triglyceride values. The rats were randomly selected for either control, 0.5 mg/day, or 1.0 mg/day continuous administration of human beta lipotropin (ER4-VTA-2) via subcutaneously implanted Alzet pumps. The pumps were filled with saline for controls, 20.835 mg/ml human beta lipotropin for the low dose group, and 41.67 mg/ml human beta lipotropin for the high dose group. The pumps were incubated overnight at 37° in saline prior to subcutaneous implantation. Body weight and food consumption was measured on days 0 through 8. Blood samples were taken the morning of day 3 for glucose, insulin, corticosterone, and triglyceride values. Rats were fasted overnight from the afternoon of day 5 to the morning of day 6. On day 6, an oral glucose tolerance test was performed. After the oral glucose tolerance test, the rats were fed ad libitum.

The Zucker animals used in this study provide a good model for type 2 diabetes. At 6 to 7 weeks of age blood glucose values and triglyceride levels are rising while insulin secretion is declining. These animals are hypercorticosteronemic and insulin resistant.

TABLE 3

ZDF Rats Treated with Human BLT

| Treatment (mg/dy BLT) | Blood Glucose (mg/dl) | | | Triglyc. (mmol/L) | | |
|---|---|---|---|---|---|---|
| | 0 | Day 2 | Day 7 | 0 | Day 2 | Day 7 |
| Control | 149 | 153 | 150 ± 8.8 | 1.9 | 2.4 | 4.1 ± 0.5 |
| 0.5 | 151 | 160 | 150 ± 5.5 | 2.0 | 2.8 | 4.0 ± 0.4 |
| 1.0 | 154 | 144 | 141 ± 5.7 | 2.0 | 2.8 | 3.6 ± 0.1 |

The results presented in Table 3 and FIG. 16 demonstrate a pronounced effect of human BLT on the ZDF rat at a dose of 1 mg per day of human BLT. At 30 minutes after the initiation of the OGTT plasma glucose levels were avg. 191±16 mg/dL in the controls and 172±5 mg/dL in the BLT-treated animals (See FIG. 16). At 60 minutes post-initiation control animals displayed glucose levels of 157±6 mg/dL, while BLT-treated animals were at 154±8 mg/dL in the BLT-treated animals.

Table 3 illustrates that blood glucose values remained lower in BLT-treated animals than in control animals, especially at the higher dose. The control animals displaed glucose values of about 150 mg/dL at 0, 2, and 7 days following the start of administration of BLT. On the other hand animals treated with 1 mg/day of human BLT averaged about 140 mg/dL at day 7, some 7% lower than the control animals. Treated animals also showed about 11% lower serum triglyceride levels than control animals (Table 3), demonstrating the insulinotropic effect of BLT treatment.

EXAMPLE 17

Human BLT Stimulates Glucose Transport in ZDF Rat Skeletal Muscle

A study was carried out to determine the effects of beta-lipotropin on glucose transport in skeletal muscle. Zucker Diabetic Fatty (ZDF/Gmi™-fa/fa) male rats were obtained from Genetic Models Inc. (Indianapolis, Ind.). The rats were maintained on Purina Formulab 5008 rat chow (Puina Mills, Inc., St. Louis, Mo.) and housed in a light controlled room with alternating 12 hour cycles of light and dark. Rats were singly housed and given free access to food and water.

To determine glucose transport in muscle tissue, the animals from Example 16 were anesthetized via an interperitoneal injection of pentabarbitol sodium (6.5 mg/100 gm body weight), and the soleus muscles isolated and divided in half. Each half of the tissue sample was washed in saline for 2 minutes, and then in gassed (95% $O_2$-5% $CO_2$) KHB with 1% BSA, 8 mM glucose, and 32 mM mannitol.

Glucose transport assays were carried out as follows.

Pre-incubation

Muscle tissue samples were transferred to 20 ml vials containing 1.8 ml gassed KHB with 1% BSA, 8 mM glucose, 32 mM mannitol, with or without 500 nM mouse beta-lipotropin. Samples were placed in a shaking waterbath for 20 hours at room temperature with two intermittent buffer changes.

After pre-incubation, muscle tissue samples were washed at 29° C. for 15 minutes under constant gassing of 95% $O_2$-5% $CO_2$. The samples were washed in vials contained 1.8 ml KHB with 40 mM mannitol, insulin (2000 uU/ml) or no insulin, and with or without beta-lipotropin (500 nM).

Muscle samples were then transferred to new vials under constant gassing of 95% $O_2$-5% $CO_2$. The incubation medium consisted of 8 mM 3-O-Methyl-Glucose (OMG), 2 mCi/ml $^3$H-3-OMG, 30 mM mannitol, 0.3 mCi/ml $^{14}$C mannitol, 2 mM Pyruvate, insulin (2000 μU/ml), and mouse beta-lipotropin. Controls lacked insulin and/or beta-lipotropin. After 10 minutes at 29° C., samples were freeze clamped and stored frozen until glucose transport could be assayed.

Glucose Transport

Muscles were trimmed to approximately 20–25 mg for digestion in 0.5 ml 1M KOH at 70° C. for 30 min. After digestion, samples were placed on ice, and a 100 μl sample was removed for glycogen analysis. To the remaining 0.4 ml sample, 0.4 ml of 1N HCl was added and the tube vortexed. Then 300 ml of the HCl-treated sample was added to 6.4 ml of scintillation fluid and the radioactivity in the sample determined in a scintillation counter.

Glucose transport was calculated on the basis of intracellular $^3$H-3-OMG accumulation using $^{14}$C Mannitol as the extracellular marker.

Glycogen Levels

To the 100 μl sample mentioned above 17 μl of glacial acetic acid was added along with 500 μl 0.3 M Sodium acetate buffer (Ph 4.8+5 mg/ml amyloglucosidase). The tubes were then incubated overnight at 37° C. The next day 50 μl of sample was placed in a 96 well plate and 200 μl of Trinder reagent (Sigma 315–100; diluted to 20 μl with water) added. The plate was incubated for 10 minutes at 37° C. and the absorbance read at a wavelength of 505 nm.

TABLE 4

Glucose Transport in Muscle Tissue from ZDF Rats Treated with Human BLT

| Treatment | 3 OMG Transport (μmol/g/10 min) |
|---|---|
| Control | .085 ± .01 |
| insulin | .080 ± |
| BLT + insulin | .113 ± .018 |

We claim:

1. A method for treating diabetes in a mammal comprising administration of a therapeutically effective amount of a naturally-occurring mammalian beta-lipotropin.

2. A method as in claim 1 wherein said beta-lipotropin is recombinant human beta-lipotropin.

3. A method as in claim 1 wherein said diabetes is Type 1 or Type 2 diabetes.

4. A method as in claim 1 wherein said mammal is a human.

5. A method for treating diabetes in a mammal comprising administration of a therapeutically effective amount of a functional fragment of a naturally-occurring mammalian beta-lipotropin wherein said fragment has the activity of lowering blood glucose.

6. A method for treating diabetes in a mammal comprising administration of a therapeutically effective amount of beta-lipotropin wherein said beta-lipotropin is human beta-lipotropin, having a sequence identified herein as SEQ ID NO:8.

7. A method for lowering blood glucose levels in a mammal by administering an effective amount of a naturally-occurring mammalian beta-lipotropin.

8. A method for treating hyperglycemia in a mammal in need thereof by administering an effective amount of a naturally-occurring mammalian beta-lipotropin.

9. A method for treating hyperinsulinemia in a mammal by administering an effective amount of a naturally-occurring mammalian beta-lipotropin.

10. A method for enhancing insulin sensitivity in a mammal by administering an effective amount of a naturally-occurring mammalian beta-lipotropin.

11. A method for treating diabetes in a mammal comprising administration of a therapeutically effective amount of beta-lipotropin wherein said beta-lipotropin is selected from the group consisting of SEQ ID NO:2, SEQ ID NO:5, SEQ ID NO:7, and SEQ ID NO:8.

12. A method for treating diabetes comprising administration of a therapeutically effective amount of at least one peptide selected from the group consisting of SEQ ID NO:9, SEQ ID NO:10, SEQ ID NO:11, SEQ ID NO:12, SEQ ID NO:13, wherein said peptide has the ability to lower blood glucose in vivo.

13. A method, for treating diabetes comprising administration of a therapeutically effective amount of a peptide having the ability to lower blood glucose in vivo, said peptide being selected from the group consisting of:

a) SEQ ID NO:9 b) SEQ ID NO:10 c) SEQ ID NO:11 d) SEQ ID NO:12 e) SEQ ID NO:13 f) SEQ ID NO:14 g) SEQ ID NO:15 h) SEQ ID NO:16 i) SEQ ID NO:17 j) SEQ ID NO:18 k) SEQ ID NO:19 l) SEQ ID NO:20 m) SEQ ID NO:21 n) SEQ ID NO:22 o) SEQ ID NO:23 p) SEQ ID NO:24 q) SEQ ID NO:25.

14. A method for alleviating the symptoms of a complication associated with diabetes in a patient in need thereof comprising administration of a therapeutically effective amount of beta-lipotropin, said complication selected from the group consisting of:

a) diabetic foot;

b) urinary tract infection; and c) peripheral vascular disease.

15. A method for treating diabetes in a mammal comprising administration of a therapeutically effective amount of an functional analog of a naturally-occurring mammalian beta-lipotropin, said analog having a single amino acid substitution in SEQ ID NO:8, and wherein said analog has a biological activity selected from the group consisting of:
   a) the ability to lower blood glucose in vivo;
   b) the ability to promote glucose uptake in vivo and/or in vitro; and
   c) the ability to enhance insulin sensitivity.

16. A method a in claim 15 wherein said activity is the ability to lower blood glucose in vivo.

17. A method a in claim 15 wherein said activity is the ability to promote glucose uptake in vivo and/or in vitro.

18. A method a in claim 15 wherein said activity is the ability to enhance insulin sensitivity.

19. A method for treating diabetes comprising administration of a therapeutically effective amount of at least one peptide selected from the group consisting of SEQ ID NO:9, SEQ ID NO:10, SEQ ID NO:11, SEQ ID NO:12, SEQ ID NO:13, wherein said peptide has the ability to enhance insulin sensitivity.

* * * * *

SEQUENCE LISTING

<160> NUMBER OF SEQ ID NOS: 35

<210> SEQ ID NO 1
<211> LENGTH: 273
<212> TYPE: DNA
<213> ORGANISM: Artificial Sequence
<220> FEATURE:

-continued

```
<223> OTHER INFORMATION: Description of Artificial Sequence:Met-Arg
      Human BLT

<400> SEQUENCE: 1
atgcgtgagc tcaccggtca gcgtcttcgc gaaggtgacg gtccggacgg tccggctgac      60
gacggtgctg gtgctcaggc agatctcgag cactccctgc tggttgctgc agaaaaaaaa     120
gacgaaggtc cgtaccgtat ggaacacttc cgttggggtt ccccgccgaa agacaaacgt     180
tacggtggtt tcatgacctc cgaaaaatcc cagaccccgc tggttaccct gttcaaaaac     240
gctatcatca aaaatgcata caaaaaaggt gaa                                   273

<210> SEQ ID NO 2
<211> LENGTH: 91
<212> TYPE: PRT
<213> ORGANISM: Artificial Sequence
<220> FEATURE:
<223> OTHER INFORMATION: Description of Artificial Sequence:Met-Arg
      Human BLT

<400> SEQUENCE: 2

Met Arg Glu Leu Thr Gly Gln Arg Leu Arg Glu Gly Asp Gly Pro Asp
 1               5                  10                  15

Gly Pro Ala Asp Asp Gly Ala Gly Ala Gln Ala Asp Leu Glu His Ser
            20                  25                  30

Leu Leu Val Ala Ala Glu Lys Lys Asp Glu Gly Pro Tyr Arg Met Glu
        35                  40                  45

His Phe Arg Trp Gly Ser Pro Pro Lys Asp Lys Arg Tyr Gly Gly Phe
    50                  55                  60

Met Thr Ser Glu Lys Ser Gln Thr Pro Leu Val Thr Leu Phe Lys Asn
 65                  70                  75                  80

Ala Ile Ile Lys Asn Ala Tyr Lys Lys Gly Glu
                85                  90

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Fusion
      protein partner

<400> SEQUENCE: 3

Met Ile Ile Gly Leu Met Val Gly Gly Val Ser Gly Ser Gly Ser Gly
 1               5                  10                  15

Ser Gly Asp Asp Asp Asp Pro
            20

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide linker

<400> SEQUENCE: 4
tatgagatct atcgaaggtc gtgagctcac cggtcagcgt gttcg                      45

<210> SEQ ID NO 5
<211> LENGTH: 114
<212> TYPE: PRT
<213> ORGANISM: Artificial Sequence
```

```
<220> FEATURE:
<223> OTHER INFORMATION: Description of Artificial Sequence: BLT fusion
      protein

<400> SEQUENCE: 5

Met Ile Ile Gly Leu Met Val Gly Val Ser Gly Ser Gly
1               5                   10                  15

Ser Gly Asp Asp Asp Pro Met Arg Glu Leu Thr Gly Gln Arg Leu
        20                  25                  30

Arg Glu Gly Asp Gly Pro Asp Gly Pro Ala Asp Asp Gly Ala Gly Ala
        35                  40                  45

Gln Ala Asp Leu Glu His Ser Leu Leu Val Ala Ala Glu Lys Lys Asp
    50                  55                  60

Glu Gly Pro Tyr Arg Met Glu His Phe Arg Trp Gly Ser Pro Pro Lys
65              70                  75                  80

Asp Lys Arg Tyr Gly Gly Phe Met Thr Ser Glu Lys Ser Gln Thr Pro
                85                  90                  95

Leu Val Thr Leu Phe Lys Asn Ala Ile Ile Lys Asn Ala Tyr Lys Lys
                100                 105                 110

Gly Glu

<210> SEQ ID NO 6
<211> LENGTH: 331
<212> TYPE: PRT
<213> ORGANISM: Artificial Sequence
<220> FEATURE:
<223> OTHER INFORMATION: Description of Artificial Sequence: GST fusion
      partner

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65              70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205
```

-continued

```
Thr Phe Gly Gly Gly Asp His Pro Pro Lys Ser Asp Leu Val Pro Arg
    210                 215                 220

Gly Ser Pro Gly Ile His Arg Asp Leu Val Pro Arg Gly Ser Ile Glu
225                 230                 235                 240

Gly Arg Glu Leu Thr Gly Gln Arg Leu Arg Glu Gly Asp Gly Pro Asp
                245                 250                 255

Gly Pro Ala Asp Asp Gly Ala Gly Ala Gln Ala Asp Leu Glu His Ser
                260                 265                 270

Leu Leu Val Ala Ala Glu Lys Lys Asp Glu Gly Pro Tyr Arg Met Glu
            275                 280                 285

His Phe Arg Trp Gly Ser Pro Pro Lys Asp Lys Arg Tyr Gly Gly Phe
        290                 295                 300

Met Thr Ser Glu Lys Ser Gln Thr Pro Leu Val Thr Leu Phe Lys Asn
305                 310                 315                 320

Ala Ile Ile Lys Asn Ala Tyr Lys Lys Gly Glu
                325                 330
```

<210> SEQ ID NO 7
<211> LENGTH: 422
<212> TYPE: PRT
<213> ORGANISM: Artificial Sequence
<220> FEATURE:
<223> OTHER INFORMATION: Description of Artificial Sequence: GST/BLT
      fusion protein

<400> SEQUENCE: 7

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile His Arg Asp Leu Val Pro Arg Gly Ser Ile Glu
225                 230                 235                 240
```

```
Gly Arg Glu Leu Thr Gly Gln Arg Leu Arg Glu Gly Asp Gly Pro Asp
                245                 250                 255

Gly Pro Ala Asp Asp Gly Ala Gly Ala Gln Ala Asp Leu Glu His Ser
            260                 265                 270

Leu Leu Val Ala Ala Glu Lys Lys Asp Glu Gly Pro Tyr Arg Met Glu
            275                 280                 285

His Phe Arg Trp Gly Ser Pro Pro Lys Asp Lys Arg Tyr Gly Gly Phe
            290                 295                 300

Met Thr Ser Glu Lys Ser Gln Thr Pro Leu Val Thr Leu Phe Lys Asn
305                 310                 315                 320

Ala Ile Ile Lys Asn Ala Tyr Lys Lys Gly Glu Met Arg Glu Leu Thr
                325                 330                 335

Gly Gln Arg Leu Arg Glu Gly Asp Gly Pro Asp Gly Pro Ala Asp Asp
            340                 345                 350

Gly Ala Gly Ala Gln Ala Asp Leu Glu His Ser Leu Leu Val Ala Ala
            355                 360                 365

Glu Lys Lys Asp Glu Gly Pro Tyr Arg Met Glu His Phe Arg Trp Gly
            370                 375                 380

Ser Pro Pro Lys Asp Lys Arg Tyr Gly Gly Phe Met Thr Ser Glu Lys
385                 390                 395                 400

Ser Gln Thr Pro Leu Val Thr Leu Phe Lys Asn Ala Ile Ile Lys Asn
                405                 410                 415

Ala Tyr Lys Lys Gly Glu
            420

<210> SEQ ID NO 8
<211> LENGTH: 89
<212> TYPE: PRT
<213> ORGANISM: Homo sapiens

<400> SEQUENCE: 8

Glu Leu Thr Gly Gln Arg Leu Arg Glu Gly Asp Gly Pro Asp Gly Pro
  1               5                  10                  15

Ala Asp Asp Gly Ala Gly Ala Gln Ala Asp Leu Glu His Ser Leu Leu
             20                  25                  30

Val Ala Ala Glu Lys Lys Asp Glu Gly Pro Tyr Arg Met Glu His Phe
         35                  40                  45

Arg Trp Gly Ser Pro Pro Lys Asp Lys Arg Tyr Gly Gly Phe Met Thr
     50                  55                  60

Ser Glu Lys Ser Gln Thr Pro Leu Val Thr Leu Phe Lys Asn Ala Ile
 65                  70                  75                  80

Ile Lys Asn Ala Tyr Lys Lys Gly Glu
                 85

<210> SEQ ID NO 9
<211> LENGTH: 49
<212> TYPE: PRT
<213> ORGANISM: Homo sapiens

<400> SEQUENCE: 9

Glu Leu Thr Gly Gln Arg Leu Arg Glu Gly Asp Gly Pro Asp Gly Pro
  1               5                  10                  15

Ala Asp Asp Gly Ala Gly Ala Gln Ala Asp Leu Glu His Ser Leu Leu
             20                  25                  30

Val Ala Ala Glu Lys Lys Asp Glu Gly Pro Tyr Arg Met Glu His Phe
         35                  40                  45
```

Arg

<210> SEQ ID NO 10
<211> LENGTH: 40
<212> TYPE: PRT
<213> ORGANISM: Homo sapiens

<400> SEQUENCE: 10

Trp Gly Ser Pro Pro Lys Asp Lys Arg Tyr Gly Gly Phe Met Thr Ser
 1               5                  10                  15

Glu Lys Ser Gln Thr Pro Leu Val Thr Leu Phe Lys Asn Ala Ile Ile
            20                  25                  30

Lys Asn Ala Tyr Lys Lys Gly Glu
        35                  40

<210> SEQ ID NO 11
<211> LENGTH: 30
<212> TYPE: PRT
<213> ORGANISM: Homo sapiens

<400> SEQUENCE: 11

Lys Asp Glu Gly Pro Tyr Arg Met Glu His Phe Arg Trp Gly Ser Pro
 1               5                  10                  15

Pro Lys Asp Lys Arg Tyr Gly Gly Phe Met Thr Ser Glu Lys
            20                  25                  30

<210> SEQ ID NO 12
<211> LENGTH: 52
<212> TYPE: PRT
<213> ORGANISM: Homo sapiens

<400> SEQUENCE: 12

Lys Asp Glu Gly Pro Tyr Arg Met Glu His Phe Arg Trp Gly Ser Pro
 1               5                  10                  15

Pro Lys Asp Lys Arg Tyr Gly Gly Phe Met Thr Ser Glu Lys Ser Gln
            20                  25                  30

Thr Pro Leu Val Thr Leu Phe Lys Asn Ala Ile Ile Lys Asn Ala Tyr
        35                  40                  45

Lys Lys Gly Glu
        50

<210> SEQ ID NO 13
<211> LENGTH: 72
<212> TYPE: PRT
<213> ORGANISM: Homo sapiens

<400> SEQUENCE: 13

Glu Leu Thr Gly Gln Arg Gln Ala Asp Leu Glu His Ser Leu Leu Val
 1               5                  10                  15

Ala Ala Glu Lys Lys Asp Glu Gly Pro Tyr Arg Met Glu His Phe Arg
            20                  25                  30

Trp Gly Ser Pro Pro Lys Asp Lys Arg Tyr Gly Gly Phe Met Thr Ser
        35                  40                  45

Glu Lys Ser Gln Thr Pro Leu Val Thr Leu Phe Lys Asn Ala Ile Ile
    50                  55                  60

Lys Asn Ala Tyr Lys Lys Gly Glu
65                  70

<210> SEQ ID NO 14

<211> LENGTH: 14
<212> TYPE: PRT
<213> ORGANISM: Homo sapiens

<400> SEQUENCE: 14

Glu Leu Thr Gly Gln Arg Leu Arg Glu Gly Asp Gly Pro Asp
 1               5                  10

<210> SEQ ID NO 15
<211> LENGTH: 14
<212> TYPE: PRT
<213> ORGANISM: Homo sapiens

<400> SEQUENCE: 15

Arg Glu Gly Asp Gly Pro Asp Gly Pro Ala Asp Asp Gly Ala
 1               5                  10

<210> SEQ ID NO 16
<211> LENGTH: 14
<212> TYPE: PRT
<213> ORGANISM: Homo sapiens

<400> SEQUENCE: 16

Gly Pro Ala Asp Asp Gly Ala Gly Ala Gln Ala Asp Leu Glu
 1               5                  10

<210> SEQ ID NO 17
<211> LENGTH: 14
<212> TYPE: PRT
<213> ORGANISM: Homo sapiens

<400> SEQUENCE: 17

Gly Ala Gln Ala Asp Leu Glu His Ser Leu Leu Val Ala Ala
 1               5                  10

<210> SEQ ID NO 18
<211> LENGTH: 14
<212> TYPE: PRT
<213> ORGANISM: Homo sapiens

<400> SEQUENCE: 18

His Ser Leu Leu Val Ala Ala Glu Lys Lys Asp Glu Gly Pro
 1               5                  10

<210> SEQ ID NO 19
<211> LENGTH: 14
<212> TYPE: PRT
<213> ORGANISM: Homo sapiens

<400> SEQUENCE: 19

Glu Lys Lys Asp Glu Gly Pro Tyr Arg Met Glu His Phe Arg
 1               5                  10

<210> SEQ ID NO 20
<211> LENGTH: 14
<212> TYPE: PRT
<213> ORGANISM: Homo sapiens

<400> SEQUENCE: 20

Tyr Arg Met Glu His Phe Arg Trp Gly Ser Pro Pro Lys Asp
 1               5                  10

<210> SEQ ID NO 21
<211> LENGTH: 14
<212> TYPE: PRT

```
<213> ORGANISM: Homo sapiens

<400> SEQUENCE: 21

Trp Gly Ser Pro Pro Lys Asp Lys Arg Tyr Gly Gly Phe Met
 1               5                  10

<210> SEQ ID NO 22
<211> LENGTH: 14
<212> TYPE: PRT
<213> ORGANISM: Homo sapiens

<400> SEQUENCE: 22

Lys Arg Tyr Gly Gly Phe Met Thr Ser Glu Lys Ser Gln Thr
 1               5                  10

<210> SEQ ID NO 23
<211> LENGTH: 14
<212> TYPE: PRT
<213> ORGANISM: Homo sapiens

<400> SEQUENCE: 23

Thr Ser Glu Lys Ser Gln Thr Pro Leu Val Thr Leu Phe Lys
 1               5                  10

<210> SEQ ID NO 24
<211> LENGTH: 14
<212> TYPE: PRT
<213> ORGANISM: Homo sapiens

<400> SEQUENCE: 24

Pro Leu Val Thr Leu Phe Lys Asn Ala Ile Ile Lys Asn Ala
 1               5                  10

<210> SEQ ID NO 25
<211> LENGTH: 12
<212> TYPE: PRT
<213> ORGANISM: Homo sapiens

<400> SEQUENCE: 25

Asn Ala Ile Ile Lys Asn Ala Tyr Lys Lys Gly Glu
 1               5                  10

<210> SEQ ID NO 26
<211> LENGTH: 89
<212> TYPE: PRT
<213> ORGANISM: Artificial Sequence
<220> FEATURE:
<223> OTHER INFORMATION: Description of Artificial Sequence: Human
      analog

<400> SEQUENCE: 26

Glu Leu Thr Gly Gln Arg Leu Arg Glu Gly Asp Gly Pro Asp Gly Pro
 1               5                  10                  15

Ala Asp Asp Gly Ala Gly Ala Gln Ala Asp Leu Glu His Ser Leu Leu
            20                  25                  30

Val Ala Ala Glu Lys Lys Asp Glu Gly Pro Tyr Arg Met Asp Lys Tyr
        35                  40                  45

Arg Tyr Ala Thr Pro Pro His Glu His Arg Tyr Ala Ala Phe Met Thr
    50                  55                  60

Ser Glu Lys Ser Gln Thr Pro Leu Val Thr Leu Phe Lys Asn Ala Ile
65                  70                  75                  80

Ile Lys Asn Ala Tyr Lys Lys Gly Glu
                85
```

<210> SEQ ID NO 27
<211> LENGTH: 89
<212> TYPE: PRT
<213> ORGANISM: Artificial Sequence
<220> FEATURE:
<223> OTHER INFORMATION: Description of Artificial Sequence: Human analog

<400> SEQUENCE: 27

```
Glu Leu Thr Gly Gln Arg Leu Arg Glu Gly Asp Gly Pro Asp Gly Pro
 1               5                  10                  15

Ala Asp Asp Gly Ala Gly Ala Gln Ala Asp Leu Glu His Ser Leu Leu
            20                  25                  30

Val Ala Ala Glu Lys Lys Asp Glu Gly Pro Tyr Arg Met Glu Lys Phe
        35                  40                  45

Arg Tyr Gly Ser Pro Pro Arg Glu Lys His Trp Gly Ala Trp Met Thr
    50                  55                  60

Ser Glu Lys Ser Gln Thr Pro Leu Val Thr Leu Phe Lys Asn Ala Ile
65                  70                  75                  80

Ile Lys Asn Ala Tyr Lys Lys Gly Glu
                85
```

<210> SEQ ID NO 28
<211> LENGTH: 89
<212> TYPE: PRT
<213> ORGANISM: Artificial Sequence
<220> FEATURE:
<223> OTHER INFORMATION: Description of Artificial Sequence: Human analog

<400> SEQUENCE: 28

```
Glu Leu Thr Gly Gln Arg Leu Arg Glu Gly Asp Gly Pro Asp Gly Pro
 1               5                  10                  15

Ala Asp Asp Gly Ala Gly Ala Gln Ala Asp Leu Glu His Ser Leu Leu
            20                  25                  30

Val Ala Ala Glu Lys Lys Asp Glu Gly Pro Tyr Arg Met Asp His Phe
        35                  40                  45

His Phe Ala Ser Pro Pro Arg Glu Lys His Tyr Gly Ala Tyr Met Thr
    50                  55                  60

Ser Glu Lys Ser Gln Thr Pro Leu Val Thr Leu Phe Lys Asn Ala Ile
65                  70                  75                  80

Ile Lys Asn Ala Tyr Lys Lys Gly Glu
                85
```

<210> SEQ ID NO 29
<211> LENGTH: 89
<212> TYPE: PRT
<213> ORGANISM: Artificial Sequence
<220> FEATURE:
<223> OTHER INFORMATION: Description of Artificial Sequence: Human analog

<400> SEQUENCE: 29

```
Glu Leu Thr Gly Gln Arg Leu Arg Glu Gly Asp Gly Pro Asp Gly Pro
 1               5                  10                  15

Ala Asp Asp Gly Ala Gly Ala Gln Ala Asp Leu Glu His Ser Leu Leu
            20                  25                  30

Val Ala Ala Glu Lys Lys Asp Glu Gly Pro Tyr Arg Met Asp His Phe
        35                  40                  45
```

```
Arg Trp Ala Ser Pro Lys Glu Arg His Phe Ala Ala Tyr Met Thr
     50                  55                  60

Ser Glu Lys Ser Gln Thr Pro Leu Val Thr Leu Phe Lys Asn Ala Ile
 65                  70                  75                  80

Ile Lys Asn Ala Tyr Lys Lys Gly Glu
                 85
```

<210> SEQ ID NO 30
<211> LENGTH: 89
<212> TYPE: PRT
<213> ORGANISM: Artificial Sequence
<220> FEATURE:
<223> OTHER INFORMATION: Description of Artificial Sequence: Human
      analog

<400> SEQUENCE: 30

```
Glu Leu Thr Gly Gln Arg Leu Arg Glu Gly Asp Gly Pro Asp Gly Pro
 1               5                  10                  15

Ala Asp Asp Gly Ala Gly Ala Gln Ala Asp Leu Glu His Ser Leu Leu
                 20                  25                  30

Val Ala Ala Glu Lys Lys Asp Glu Gly Pro Tyr Arg Met Asp Lys Tyr
             35                  40                  45

Arg Phe Gly Thr Pro Pro Arg Glu Lys Arg Phe Ala Gly Tyr Met Thr
     50                  55                  60

Ser Glu Lys Ser Gln Thr Pro Leu Val Thr Leu Phe Lys Asn Ala Ile
 65                  70                  75                  80

Ile Lys Asn Ala Tyr Lys Lys Gly Glu
                 85
```

<210> SEQ ID NO 31
<211> LENGTH: 89
<212> TYPE: PRT
<213> ORGANISM: Artificial Sequence
<220> FEATURE:
<223> OTHER INFORMATION: Description of Artificial Sequence: Human
      analog

<400> SEQUENCE: 31

```
Glu Leu Thr Gly Gln Arg Leu Arg Glu Gly Asp Gly Pro Asp Gly Pro
 1               5                  10                  15

Ala Asp Asp Gly Ala Gly Ala Gln Ala Asp Leu Glu His Ser Leu Leu
                 20                  25                  30

Val Ala Ala Glu Lys Lys Asp Glu Gly Pro Tyr Arg Met Asp Arg Trp
             35                  40                  45

Arg Trp Ala Ser Pro Pro Arg Glu Lys His Tyr Gly Ala Trp Met Thr
     50                  55                  60

Ser Glu Lys Ser Gln Thr Pro Leu Val Thr Leu Phe Lys Asn Ala Ile
 65                  70                  75                  80

Ile Lys Asn Ala Tyr Lys Lys Gly Glu
                 85
```

<210> SEQ ID NO 32
<211> LENGTH: 89
<212> TYPE: PRT
<213> ORGANISM: Artificial Sequence
<220> FEATURE:
<223> OTHER INFORMATION: Description of Artificial Sequence: Human
      analog

<400> SEQUENCE: 32

```
Glu Leu Thr Gly Gln Arg Leu Arg Glu Gly Asp Gly Pro Asp Gly Pro
```

```
              1               5                  10                 15
Ala Asp Asp Gly Ala Gly Ala Gln Ala Asp Leu Glu His Ser Leu Leu
                20                  25                 30

Val Ala Ala Glu Lys Lys Asp Glu Gly Pro Tyr Arg Met Glu Arg Trp
            35                  40                 45

Lys Phe Ala Thr Pro Pro His Asp His Lys Trp Gly Gly Phe Met Thr
        50                  55                 60

Ser Glu Lys Ser Gln Thr Pro Leu Val Thr Leu Phe Lys Asn Ala Ile
65                  70                  75                  80

Ile Lys Asn Ala Tyr Lys Lys Gly Glu
                85
```

<210> SEQ ID NO 33
<211> LENGTH: 89
<212> TYPE: PRT
<213> ORGANISM: Artificial Sequence
<220> FEATURE:
<223> OTHER INFORMATION: Description of Artificial Sequence: Human
      analog

<400> SEQUENCE: 33

```
Glu Leu Thr Gly Gln Arg Leu Arg Glu Gly Asp Gly Pro Asp Gly Pro
1               5                  10                 15

Ala Asp Asp Gly Ala Gly Ala Gln Ala Asp Leu Glu His Ser Leu Leu
                20                  25                 30

Val Ala Ala Glu Lys Lys Asp Glu Gly Pro Tyr Arg Met Asp Lys Trp
            35                  40                 45

Arg Trp Ala Ser Pro Pro Lys Glu His Arg Trp Gly Gly Tyr Met Thr
        50                  55                 60

Ser Glu Lys Ser Gln Thr Pro Leu Val Thr Leu Phe Lys Asn Ala Ile
65                  70                  75                  80

Ile Lys Asn Ala Tyr Lys Lys Gly Glu
                85
```

<210> SEQ ID NO 34
<211> LENGTH: 89
<212> TYPE: PRT
<213> ORGANISM: Artificial Sequence
<220> FEATURE:
<223> OTHER INFORMATION: Description of Artificial Sequence: Human
      analog

<400> SEQUENCE: 34

```
Glu Leu Thr Gly Gln Arg Leu Arg Glu Gly Asp Gly Pro Asp Gly Pro
1               5                  10                 15

Ala Asp Asp Gly Ala Gly Ala Gln Ala Asp Leu Glu His Ser Leu Leu
                20                  25                 30

Val Ala Ala Glu Lys Lys Asp Glu Gly Pro Tyr Arg Met Asp His Phe
            35                  40                 45

Lys Tyr Ala Ser Pro Pro His Glu Arg His Phe Gly Ala Trp Met Thr
        50                  55                 60

Ser Glu Lys Ser Gln Thr Pro Leu Val Thr Leu Phe Lys Asn Ala Ile
65                  70                  75                  80

Ile Lys Asn Ala Tyr Lys Lys Gly Glu
                85
```

<210> SEQ ID NO 35
<211> LENGTH: 89
<212> TYPE: PRT

-continued

```
<213> ORGANISM: Artificial Sequence
<220> FEATURE:
<223> OTHER INFORMATION: Description of Artificial Sequence: Human
      analog

<400> SEQUENCE: 35

Glu Leu Thr Gly Gln Arg Leu Arg Glu Gly Asp Gly Pro Asp Gly Pro
 1               5                  10                  15

Ala Asp Asp Gly Ala Gly Ala Gln Ala Asp Leu Glu His Ser Leu Leu
                20                  25                  30

Val Ala Ala Glu Lys Lys Asp Glu Gly Pro Tyr Arg Met Glu Lys Phe
            35                  40                  45

Lys Trp Ala Thr Pro Pro His Glu Arg Arg Tyr Gly Ala Tyr Met Thr
     50                  55                  60

Ser Glu Lys Ser Gln Thr Pro Leu Val Thr Leu Phe Lys Asn Ala Ile
 65                  70                  75                  80

Ile Lys Asn Ala Tyr Lys Lys Gly Glu
                 85
```